United States Patent
Lou et al.

(10) Patent No.: US 9,689,813 B2
(45) Date of Patent: Jun. 27, 2017

(54) DETECTING GAPS BETWEEN FASTENERS AND OPENINGS

(71) Applicant: The Boeing Company, Chicago, IL (US)

(72) Inventors: Taisia Tsukruk Lou, St. Louis, MO (US); William Talion Edwards, Wentzville, MO (US); Gregory Paul Saguto, St. Charles, MO (US)

(73) Assignee: THE BOEING COMPANY, Chicago, IL (US)

( * ) Notice: Subject to any disclaimer, the term of this patent is extended or adjusted under 35 U.S.C. 154(b) by 291 days.

(21) Appl. No.: 14/633,379

(22) Filed: Feb. 27, 2015

(65) Prior Publication Data
US 2016/0252468 A1 Sep. 1, 2016

(51) Int. Cl.
*G01N 23/203* (2006.01)

(52) U.S. Cl.
CPC ..... *G01N 23/203* (2013.01); *G01N 2223/053* (2013.01); *G01N 2223/3037* (2013.01); *G01N 2223/629* (2013.01); *G01N 2223/631* (2013.01)

(58) Field of Classification Search
CPC ............... G01N 23/203; G01N 2223/053
USPC ............................................. 378/86–90
See application file for complete search history.

(56) References Cited

U.S. PATENT DOCUMENTS

| | | | |
|---|---|---|---|
| 6,421,418 B1 * | 7/2002 | Schulte | G01B 15/02 378/86 |
| 7,508,910 B2 | 3/2009 | Safai et al. | |
| 7,623,626 B2 | 11/2009 | Safai et al. | |
| 7,649,976 B2 | 1/2010 | Georgeson et al. | |
| 8,094,781 B1 | 1/2012 | Safai et al. | |
| 8,396,187 B2 * | 3/2013 | Safai | G01N 23/203 378/197 |
| 8,503,610 B1 * | 8/2013 | Safai | G01N 23/04 378/70 |
| 8,761,338 B2 | 6/2014 | Safai | |
| 8,855,268 B1 * | 10/2014 | Safai | G01N 23/203 378/130 |
| 8,873,711 B2 | 10/2014 | Engelbart et al. | |
| 8,879,688 B2 * | 11/2014 | Safai | G01N 23/20008 378/86 |
| 9,031,188 B2 * | 5/2015 | Belcher | G01N 23/203 378/58 |
| 9,036,781 B1 * | 5/2015 | Safai | G01N 23/00 378/86 |
| 9,128,030 B1 * | 9/2015 | Safai | G01N 23/203 |
| 9,151,721 B2 * | 10/2015 | Safai | G01N 23/203 |

(Continued)

OTHER PUBLICATIONS

Bougeant, "Alternative Techniques of Backscatter Radiography: Snapshot Aperture Backscatter Radiography and Collimated Segmented Detector Scatter X-Ray Imaging," Masters Thesis, University of Florida, Aug. 2009, 111 pages.

(Continued)

*Primary Examiner* — Allen C. Ho
(74) *Attorney, Agent, or Firm* — Yee & Associates, P.C.

(57) ABSTRACT

A method and apparatus are presented. X-rays are directed at a workpiece. The workpiece includes a fastener installed in an opening. Backscatter is received from the workpiece. It is determined if the fastener installed in the opening has an out of tolerance gap using the backscatter. An output is generated if the fastener installed in the opening has the out of tolerance gap.

20 Claims, 12 Drawing Sheets

(56) References Cited

U.S. PATENT DOCUMENTS

| | | | |
|---|---|---|---|
| 9,506,879 B2 * | 11/2016 | Engelbart | ............ G01N 17/043 |
| 2013/0255385 A1 | 10/2013 | Edwards et al. | |
| 2013/0336455 A1 | 12/2013 | Engelbart et al. | |

OTHER PUBLICATIONS

Engelbart et al., "Method and System for Non-Destructively Evaluating a Hidden Workpiece," U.S. Appl. No. 14/505,043, filed Oct. 2, 2014, 34 pages.

\* cited by examiner

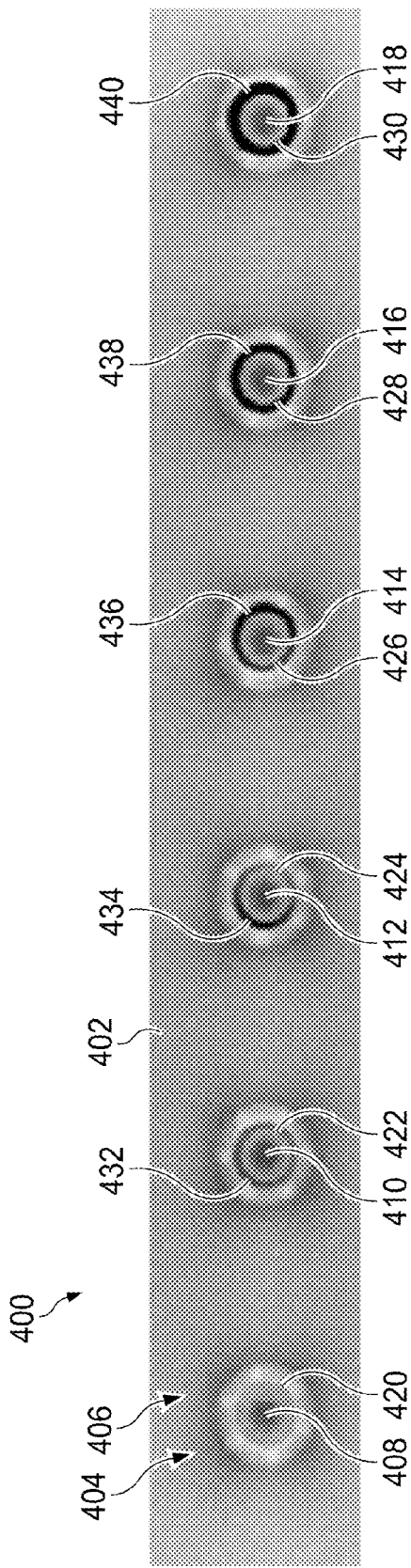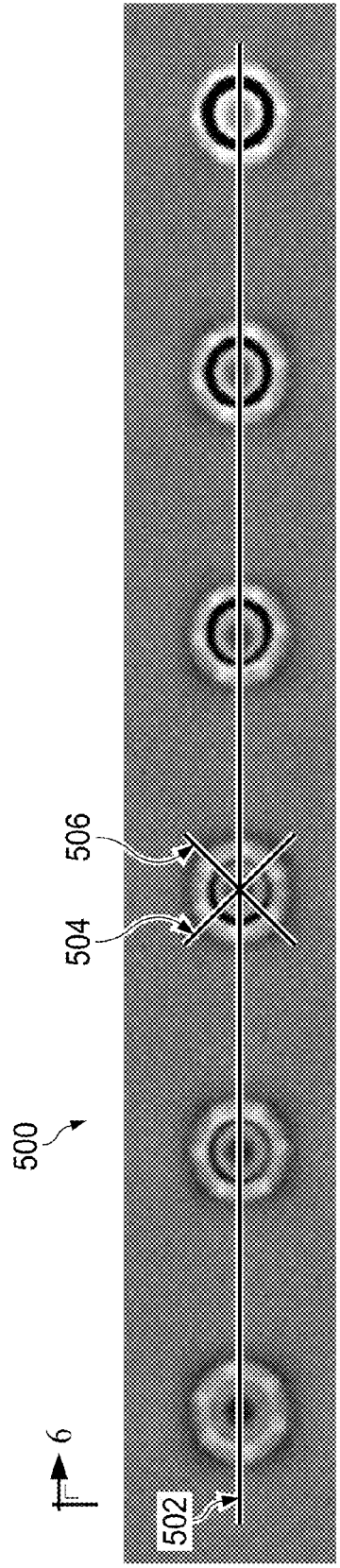
FIG. 4
FIG. 5

DETECTING GAPS BETWEEN FASTENERS AND OPENINGS

BACKGROUND INFORMATION

1. Field

The present disclosure relates generally to inspection systems, and in particular, to backscatter inspection systems. More particularly, the present disclosure relates to detecting a gap. Still more particularly, the present disclosure relates to a method and apparatus for detecting a gap between a fastener and an opening.

2. Background

A fastener may be inserted through an opening in a first object and a second object to connect the two objects in a workpiece. The mechanical interaction between the fastener and the opening may be called the fit. The fit may be affected by the size of the opening and the size of the fastener. Types of fits may include clearance fit, interference fit, or other desirable types of fit.

There may be variation in forming the openings in the first object and the second object. An allowable or expected amount of variation in a process may be called the tolerance of the process. There may be a tolerance for forming the opening. There may also be a tolerance for forming the fastener. As a result, there may be a tolerance for the gap between the fastener and the opening.

Further, a variety of sizes of fasteners may be present in a manufacturing environment. In some cases, a fastener having an undesirable size may be inadvertently selected and inserted into an opening. At least one of the tolerance of the opening, the size of the fastener, or the tolerance of the fastener may cause the fit between the fastener and the opening to be undesirable. In some cases, at least one of the tolerance of the opening, the size of the fastener, or the tolerance of the fastener may cause a gap between the fastener and the opening. In some cases, this gap may be out of tolerance.

After assembly of the workpiece, layers of material may be present over the fastener. Disassembly of the workpiece including removal of any layers over the fastener may be necessary to determine if a gap is present between the fastener and the opening. Further, disassembly of the workpiece including removal of any layers over the fastener may be necessary to determine if a gap between the fastener and the opening is out of tolerance.

Disassembly of the workpiece may take an undesirable amount of time. Further, disassembly of the workpiece may result in undesirable effects to the quality of the workpiece. Yet further, disassembly of the workpiece may have undesirable manufacturing costs.

Therefore, it would be desirable to have a method and apparatus that take into account at least some of the issues discussed above, as well as other possible issues. One issue may be to provide a method of detecting gaps without disassembly of the workpiece. Another issue may be to determine a size of a gap between a fastener and an opening without disassembly of the workpiece. Yet another issue may be to determine if a gap between a fastener and an opening is out of tolerance.

SUMMARY

An illustrative embodiment of the present disclosure provides a method. X-rays are directed at a workpiece. The workpiece includes a fastener installed in an opening. Backscatter is received from the workpiece. It is determined if the fastener installed in the opening has an out of tolerance gap using the backscatter. An output is generated if the fastener installed in the opening has the out of tolerance gap.

Another illustrative embodiment of the present disclosure provides a method. X-rays are directed at a workpiece. The workpiece includes a fastener installed in an opening. Backscatter is received from the workpiece. An estimated gap associated with the fastener in the opening is determined using the backscatter.

Yet another illustrative embodiment of the present disclosure provides an apparatus. The apparatus is comprised of x-ray inspection equipment and a processor unit. The x-ray inspection equipment has an x-ray generation system for directing x-rays at a workpiece and a detector system for receiving backscatter from the workpiece. The workpiece includes a fastener installed in an opening. The processor unit determines if the fastener installed in the opening has an out of tolerance gap using the backscatter. The processor unit also generates an output if the fastener installed in the opening has the out of tolerance gap.

The features and functions can be achieved independently in various embodiments of the present disclosure or may be combined in yet other embodiments in which further details can be seen with reference to the following description and drawings.

BRIEF DESCRIPTION OF THE DRAWINGS

The novel features believed characteristic of the illustrative embodiments are set forth in the appended claims. The illustrative embodiments, however, as well as a preferred mode of use, further objectives and features thereof, will best be understood by reference to the following detailed description of an illustrative embodiment of the present disclosure when read in conjunction with the accompanying drawings, wherein:

FIG. 4 is an illustration of a raw data image in accordance with an illustrative embodiment;

FIG. 5 is an illustration of an image in accordance with an illustrative embodiment;

DETAILED DESCRIPTION

Figure 1:
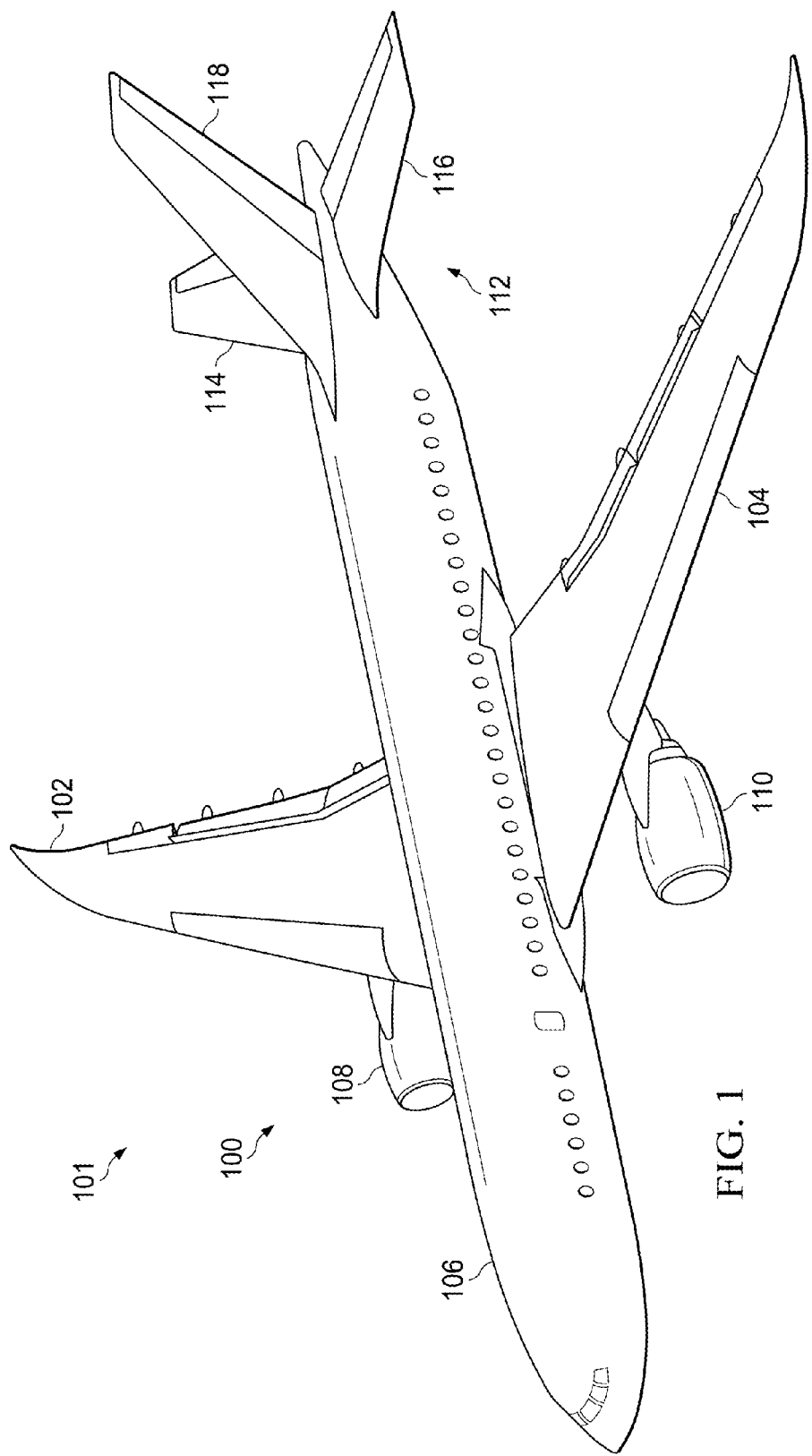
FIG. 1 is an illustration of an aircraft in which an illustrative embodiment may be implemented.

The different advantageous embodiments recognize and take into account a number of different considerations. As used herein, "a number of items" means one or more items. For example, "a number of different considerations" means one or more considerations.

The different illustrative embodiments recognize and take into account that out of tolerance conditions may result from undesirable drilling of a number of openings. For example, a hole with an undesirably large diameter may result in an out of tolerance condition. As another example, a double drilled opening may result in an out of tolerance condition. Yet further, an elongated opening may result in an out of tolerance condition. Further, the position of a fastener within an opening may result in an out of tolerance condition. For example, a fastener may not be centered within an opening.

The different illustrative embodiments recognize and take into account that accessing a surface within a workpiece by disassembling the workpiece may be more expensive or time-consuming than desired. The different illustrative embodiments further recognize and take into account that even when a surface is accessible for testing and inspection, accessing an opposite side of the surface may be more difficult or time-consuming than desired.

The different illustrative embodiments recognize and take into account that a backscatter x-ray system is an example of a nondestructive inspection system (NDI) that uses x-rays to inspect an object. A backscatter x-ray system may include an x-ray tube, a collimator, and a detector. The x-ray tube generates and emits x-rays. The collimator filters these x-rays to form an x-ray beam using a portion of the x-rays that travel substantially parallel to a specified direction.

When the x-ray beam encounters the object, some or all of the x-rays in the x-ray beam are scattered by the object. In particular, the x-rays may be scattered off of the surface of the object and/or the subsurface of the object. The scattered x-rays are referred to as backscatter. The detector detects some or all of this backscatter. The detected backscatter may be used to generate image data for the object that can be used to form one or more images of the object. For example, the backscatter detected when the x-ray beam is directed at a particular location on the object may be used to generate an intensity value for a pixel in an image that corresponds to that particular location on the object.

The different illustrative embodiments also recognize and take into account that the amount of backscatter detected by a detector determines the intensity value for a pixel in an image corresponding to the location at which the x-ray beam encounters the object. The intensity values for the pixels in an image may determine the level of contrast in the image and the level of detail in the image.

The different illustrative embodiments recognize and take into account that conventional backscatter x-ray systems were designed for large object detection. The different illustrative embodiments recognize and take into account that conventional backscatter x-ray systems were not designed for non-destructive evaluation which may require a higher degree of accuracy. The illustrative embodiments recognize and take into account that the scanning speed, standoff, x-ray source, and detector resolution may each contribute to the contrast of images from conventional backscatter x-ray systems. The illustrative examples recognize and take into account that based on past results, it was believed that currently available backscatter x-ray systems may not have the desired amount of contrast for identifying or quantifying out of tolerance conditions of fasteners. For example, it was previously believed that the gaps typically present between interference fit fasteners and their respective openings was below the spatial resolution of backscatter x-ray systems.

Resolution of backscatter x-ray systems was conventionally believed to be affected by the size of a collimated x-ray beam leaving the x-ray system and the distance away from the object under inspection. The size of the collimated x-ray beam may be controlled by the aperture of the collimator. The materials of a collimator may be difficult to machine. The collimator has a cross-section capable of attenuating all x-rays not passing through the aperture. The cross-sections which may attenuate the x-rays not passing through the aperture may cause machining precision holes for apertures smaller than 0.5 millimeters extremely difficult. As a result, resolution of conventional backscatter x-ray systems may be limited.

Resolution may be recovered by oversampling of the object and average. Even using oversampling and averaging to increase the resolution, it was previously believed that the resolving capability of backscatter x-ray systems was larger than about 0.75 millimeters.

The different illustrative embodiments further recognize and take into account that a gap between a fastener and an opening may be small. As an example, a gap may be only a fraction of a millimeter. In some examples, a gap may be less than 0.75 millimeters. Further, the different illustrative embodiments recognize and take into account that the difference between an out of tolerance condition and a desirable condition for a fastener within an opening may be a fraction of a millimeter.

Thus, the different illustrative embodiments provide a method. X-rays are directed at a workpiece. The workpiece includes a fastener installed in an opening. Backscatter is received from the workpiece. It is determined if the fastener installed in the opening has an out of tolerance gap using the backscatter. An output is generated if the fastener installed in the opening has an out of tolerance gap.

In the illustrative examples, an out of tolerance gap may be determined in at least one of three ways. As used herein, the phrase "at least one of," when used with a list of items, means different combinations of one or more of the listed items may be used and only one of each item in the list may be needed. For example, "at least one of item A, item B, or item C" may include, without limitation, item A, item A and item B, or item B. This example also may include item A, item B, and item C or item B and item C. Of course, any combinations of these items may be present. In other examples, "at least one of" may be, for example, without limitation, two of item A; one of item B; and ten of item C; four of item B and seven of item C; or other suitable combinations. The item may be a particular object, thing, or a category. In other words, "at least one of" means any combination of items and number of items may be used from the list but not all of the items in the list are required.

First, an out of tolerance gap may be determined by analyzing an image or a raw data image formed using backscatter from the workpiece. An operator or a processor unit may analyze the image or raw data image and determine if an out of tolerance condition exists in the image or raw data image. In some examples, the image or raw data image may be compared to an image or raw data image of a standard with known gap sizes. Second, an out of tolerance gap may be determined by generating a plot profile using the backscatter from the workpiece. If a lowest point of a valley in the plot profile is lower than a pre-selected limit, an out of tolerance condition may exist. In some examples, the pre-selected limit may be selected based on a standard with known gap sizes. If a difference between a lowest point of a valley in the plot profile and a background is above a limit, an out of tolerance condition may exist. Third, a ratio may be calculated using the backscatter from the workpiece. More specifically, the ratio may be calculated by first forming a plot profile and calculating a ratio based on a lowest point of a valley in the plot profile. The ratio may be inputted into a ratio to estimated gap size equation to form an estimated gap. If the estimated gap is an undesirable value, an out of tolerance condition may be determined. In some examples, the ratio to estimated gap size equation may be calculated based on a standard with known gap sizes. By inputting the ratio from the workpiece into the equation, the estimated gap size for the opening in the workpiece may be determined.

The first two ways of identifying an out of tolerance gap may be described as qualitative methods. For example, an out of tolerance gap may be identified; however, the value of the gap is not determined. The last way of identifying an out of tolerance gap may be described as a quantitative method. In the last way, the estimated gap may be determined.

With reference now to the figures, and in particular, with reference to FIG. 1, an illustration of an aircraft is depicted in which an illustrative embodiment may be implemented. In this illustrative example, aircraft 100 is manufactured in manufacturing environment 101. As depicted, aircraft 100 has wing 102 and wing 104 attached to body 106. Aircraft 100 includes engine 108 attached to wing 102 and engine 110 attached to wing 104.

Body 106 has tail section 112. Horizontal stabilizer 114, horizontal stabilizer 116, and vertical stabilizer 118 are attached to tail section 112 of body 106. Out of tolerance gaps between fasteners and openings in any of wing 102, wing 104, body 106, or other components of aircraft 100 may be detected using the illustrative embodiments.

This illustration of aircraft 100 is provided for purposes of illustrating one environment in which the different illustrative embodiments may be implemented. The illustration of aircraft 100 in FIG. 1 is not meant to imply architectural limitations to the manner in which different illustrative embodiments may be implemented. For example, an illustrative embodiment may be applied to other types of platforms. The platform may be, for example, a mobile platform, a stationary platform, a land-based structure, an aquatic-based structure, or a space-based structure. More specifically, the platform, may be a surface ship, a tank, a personnel carrier, a train, a spacecraft, a space station, a satellite, a submarine, an automobile, a power plant, a bridge, a dam, a house, a manufacturing facility, a building, or other suitable platforms.

Figure 2:
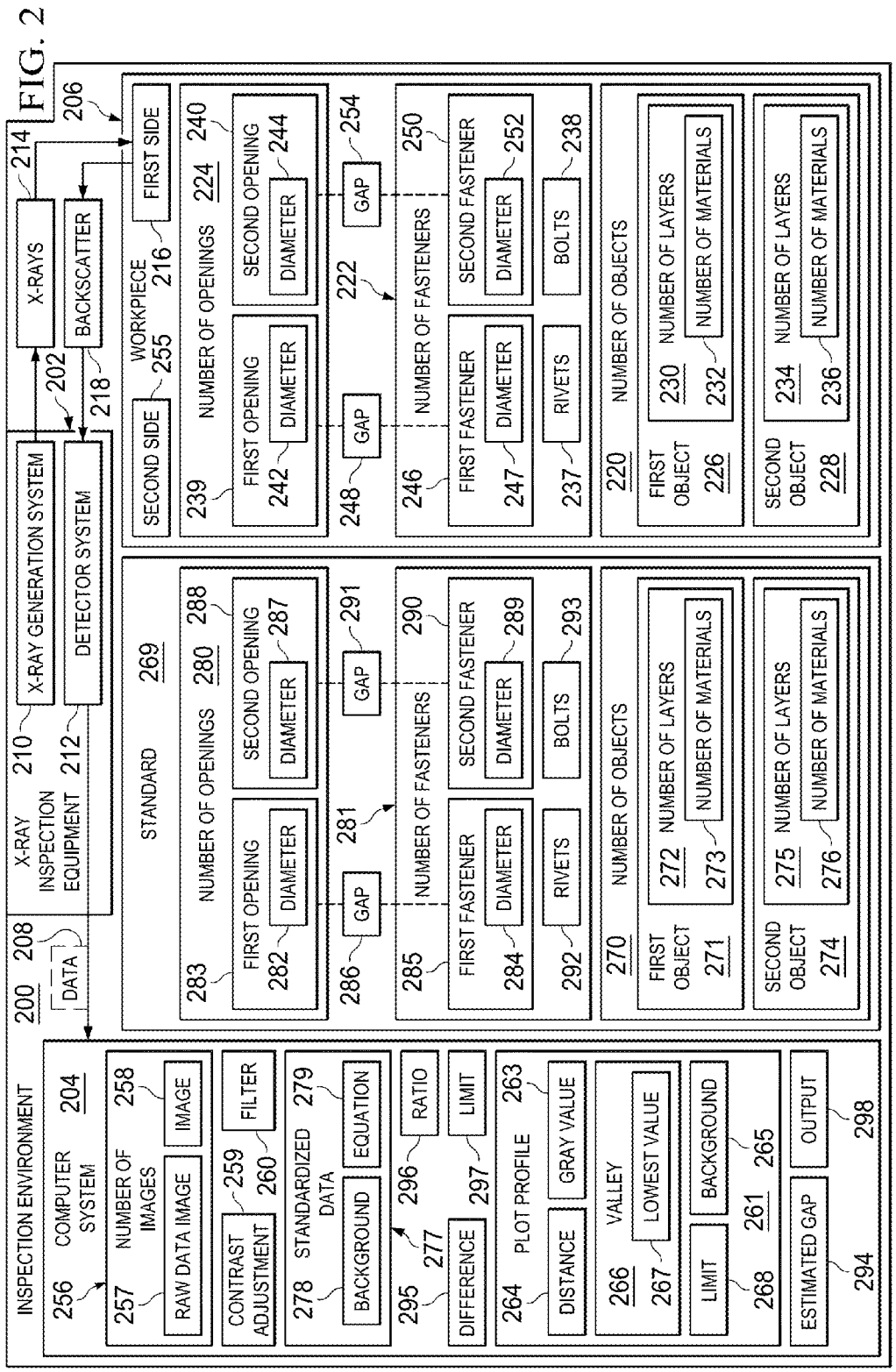
FIG. 2 is an illustration of an inspection environment in the form of a block diagram in accordance with an illustrative embodiment.

Turning now to FIG. 2, an illustration of an inspection environment in the form of a block diagram is depicted in accordance with an illustrative embodiment. In these illustrative examples, inspection environment 200 includes x-ray inspection equipment 202, computer system 204, and workpiece 206.

X-ray inspection equipment 202 is one example of a nondestructive inspection (NDI) system. As used herein, a "nondestructive inspection system" is a system configured to inspect an object, such as workpiece 206, without causing any undesired effects to the object. In particular, a nondestructive inspection system is configured to inspect an object without causing any physical alterations to the object.

In these illustrative examples, x-ray inspection equipment 202 may be used to inspect workpiece 206. Workpiece 206 may be selected from any number of different types of objects. For example, without limitation, workpiece 206 may take the form of a mobile platform, a stationary platform, an air-based structure, a land-based structure, an aquatic-based structure, a space-based structure, or some other suitable type of structure. More specifically, workpiece 206 may be an aircraft, a ship, a tank, a personnel carrier, a spacecraft, a space station, a satellite, a submarine, a vehicle, a manmade structure, a building, or some other suitable type of object.

In some cases, workpiece 206 may be a part in another object. For example, in some cases, workpiece 206 may be a section of a fuselage for an aircraft, a wing, a fuel tank, a structural support on a bridge, a section of a space station, the hull of a ship, a skin panel, a wall, a door, or some other suitable type of part.

X-ray inspection equipment 202 generates data 208 for workpiece 206 during inspection of workpiece 206. Data 208 may include, for example, without limitation, image data for workpiece 206. X-ray inspection equipment 202 sends data 208 to computer system 204. Computer system 204 is configured to receive and process data 208 generated by x-ray inspection equipment 202.

In this illustrative example, x-ray inspection equipment 202 includes x-ray generation system 210 and detector system 212. In these illustrative examples, x-ray generation system 210 may comprise components such as a radiation source and a collimator. In one illustrative example, x-ray generation system 210 may include an x-ray tube configured to generate and emit x-rays 214. X-rays 214 may be directed towards first side 216 of workpiece 206. X-ray generation system 210 may also have a collimator. A collimator is a device configured to filter the plurality of x-rays from the x-ray tube such that only x-rays 214 are allowed to pass through the collimator. In one illustrative example, a collimator may take the form of a rotatable wheel having a number of apertures.

Depending on the implementation, computer system 204 may be configured to control at least one of x-ray generation system 210 or detector system 212. For example, computer system 204 may send commands to x-ray generation system 210 to control the steering of x-rays 214.

Detector system 212 is configured to detect backscatter 218 formed in response to x-rays 214 encountering workpiece 206. Backscatter 218 may be formed in response to at least a portion of x-rays 214 being scattered when x-rays 214 encounter first side 216 of workpiece 206 and/or the subsurface of workpiece 206.

Detector system 212 generates data 208 in response to detecting backscatter 218. Data 208 may include image data. Image data in data 208 may include, for example, an intensity value for a pixel corresponding to each of a plurality of locations on workpiece 206 at which x-rays 214 were directed.

Detector system 212 sends data 208 to computer system 204 for processing. Detector system 212 may send data 208 to computer system 204 using a wireless communications link, a wired communications link, an optical communications link, or some other suitable type of communications link.

Computer system 204 may include one or more computers, depending on the implementation. When more than one computer is present in computer system 204, these computers may be in communication with each other using a medium such as a network. The network may employ wired communications links, wireless communications links, or other suitable types of links for exchanging information.

Workpiece 206 may include number of objects 220 joined together by number of fasteners 222 extending through number of openings 224. In some illustrative examples, number of objects 220 include first object 226 and second object 228. First object 226 may include number of layers 230 of number of materials 232. Second object 228 may include number of layers 234 of number of materials 236.

Number of openings 224 extend through both first object 226 and second object 228. Number of fasteners 222 may be inserted into number of openings 224. Number of fasteners 222 may take the form of rivets 237 or bolts 238. In some illustrative examples, number of fasteners 222 may instead take the form of rods, bars, welding material, or any other type of fasteners. Number of openings 224 may include first opening 239 and second opening 240. First opening 239 may have diameter 242. Second opening 240 may have diameter 244.

First fastener 246 may be installed in first opening 239. First fastener 246 may have diameter 247. First fastener 246 and first opening 239 may form gap 248. The size of gap 248 may be influenced by diameter 242 and diameter 247. In some illustrative examples, gap 248 may be a fraction of a millimeter. Second fastener 250 may be installed in second opening 240. Second fastener may have diameter 252. Second fastener 250 and second opening 240 may form gap 254. The size of gap 254 may be influenced by diameter 244 and diameter 252. In some illustrative examples, gap 254 may be a fraction of a millimeter.

To determine whether gap 248 or gap 254 is out of tolerance, x-ray inspection equipment 202 may direct x-rays 214 at first side 216 of workpiece 206. Detector system 212 generates data 208 in response to detecting backscatter 218. Unlike conventional non-destructive inspection equipment, detector system 212 receives backscatter 218 from first side 216 of workpiece 206. Detector system 212 need not access second side 255 of workpiece 206. Data 208 may be used to determine if an out of tolerance condition exists between number of openings 224 and number of fasteners 222 in workpiece 206.

For example, data 208 may be used to determine whether either gap 248 or gap 254 is out of tolerance. In one illustrative example, computer system 204 uses data 208 to form number of images 256 of workpiece 206. Number of images 256 may be analyzed by at least one of computer system 204 or a human operator to detect the presence of, and identify the location of, an out of tolerance condition between number of openings 224 and number of fasteners 222 in workpiece 206. In some illustrative examples, at least one of computer system 204 or a human operator may use number of images 256 directly to identify an out of tolerance condition. For example, at least one of a human operator or computer system 204 may identify an out of tolerance condition by the shading or shape of portions of number of images 256. The darker a pixel in number of images 256, the lower a backscatter count for that pixel.

Number of images 256 may include raw data image 257 and image 258. Raw data image 257 may be formed using data 208 from x-ray inspection equipment 202. In some illustrative examples, raw data image 257 may be formed from data 208 and contrast adjustment 259.

Image 258 may be an image formed from data 208 using image processing functions. In some illustrative examples, contrast adjustment 259 may be performed on raw data image 257 to form image 258. In another illustrative example, image 258 may be formed by applying filter 260 to raw data image 257. Filter 260 may be any type of image filter. For example, filter 260 may be a bandpass filter, a lowpass filter, a highpass filter, or other desirable type of filter.

An undesirable value for gap 248 or gap 254 may be visible in at least one of raw data image 257 or image 258. For example, an operator may identify an out of tolerance condition for gap 248 or gap 254 in at least one of raw data image 257 or image 258. An out of tolerance condition in at least one of raw data image 257 or image 258 may be seen as a black ring. As another example, computer system 204 may identify an out of tolerance condition in at least one of raw data image 257 or image 258.

In some illustrative examples, plot profile 261 may be formed from number of images 256. Plot profile 261 may be a plot of gray value 263 versus distance 264. Gray value 263 may be data for a color of a single pixel. Gray value 263 may be a numerical value assigned to a single pixel. Gray value 263 may be related to backscatter counts for that pixel. Gray value 263 may be a specific shade of gray.

Plot profile 261 may represent only a single line of data from number of images 256. In some illustrative examples, several plot profiles may be formed from an image of number of images 256 to determine different values for a single gap along different positions of an opening.

Distance 264 may be a distance along a line through number of images 256. For example, distance 264 may be a distance along a line through image 258. Plot profile 261 may include background 265 and valley 266. Background 265 may be an average value for locations which do not include an opening or a fastener in workpiece 206. In some illustrative examples, an average value may be in the form of at least one of a mean, a median, a mode, or other desirable statistical measure to set background 265. The locations represented by background 265 may have normal variations in gray value 263 across distance 264. Valley 266 may be a dip or low area in plot profile 261. Valley 266 may be formed by decreasing backscatter counts. Valley 266 may be a result of a fastener or a gap. If lowest value 267 of valley 266 falls below limit 268, valley 266 may indicate an out of tolerance value. Thus, plot profile 261 may be used to determine a presence of an out of tolerance gap. In some illustrative examples, lowest value 267 may be a lowest value of the whole of valley 266. In some illustrative examples, the absolute lowest values of valley 266 may be "cut-off" or disregarded. Disregarding the absolute lowest values may be performed to remove extreme points which may be noise. In these illustrative examples, lowest value 267 may be the lowest value in a section of valley 266 to be analyzed. For example, the lowest 10% of valley 266 may be disregarded such that lowest value 267 is a 90% value. These percentages may vary. For example, lowest value 267 may be a 75% value. In some illustrative examples, all values of valley 266 below an extreme lower limit may be disregarded regardless of the percentage value of valley 266. In some illustrative examples, the value of lowest value 267 may instead be a second lowest value instead of the absolute lowest value.

Limit 268 may be a predetermined value. Limit 268 may be determined from inspection of standard 269.

Standard 269 may be an item having the same layup as workpiece 206. For example, number of objects 270 of standard 269 may have the same material composition as number of objects 220. First object 271, having number of layers 272 formed of number of materials 273, may be substantially the same as first object 226, having number of layers 230 formed of number of materials 232. Further, second object 274, having number of layers 275 formed of number of materials 276, may be substantially the same as second object 228, having number of layers 234 formed of number of materials 236. Standard 269 may be a model to perform comparative evaluations. As a result, a number of out of tolerance conditions may be intentionally formed in standard 269. In some illustrative examples, a number of different out of tolerance conditions may be intentionally formed in standard 269.

Limit 268 may be a predetermined value based on the value of out of tolerance conditions in standard 269. For example, limit 268 may be a value under which an out of tolerance condition is likely. Limit 268 may be selected based on a desirable percentage of at least one of true positives, true negatives, false negatives, or false positives. Limit 268 may be different for different sized openings, different sized fasteners, or different material compositions of workpiece 206. Limit 268 may be selected based on standardized data 277.

Further, standard 269 may be used to form standardized data 277. Standardized data 277 may include background 278 and equation 279. In some illustrative examples, standardized data 277 may also include a number of limits, such as limit 268. In some illustrative examples, standardized data 277 may also include images of standard 269 formed from an inspection of standard 269. Background 278 may be an average value for locations which do not include an opening or a fastener in standard 269. In some illustrative examples, an average value may be in the form of at least one of a mean, a median, a mode, or other desirable statistical measure to set background 278. The locations represented by background 278 may have normal variations in gray value 263.

Equation 279 may be determined using data from inspecting standard 269. For example, sizes of gaps between number of openings 280 and number of fasteners 281 may be determined by directly measuring the size of each fastener of number of fasteners 281 and the size of each opening in number of openings 280. Diameter 282 of first opening 283 may be directly measured using at least one of a probe, a gauge, a micrometer, or other desirable measuring device. Diameter 284 of first fastener 285 may be directly measured using a gauge, a micrometer, or other desirable measuring device. The difference between diameter 282 of first opening 283 and diameter 284 of first fastener 285 may be described as gap 286. Diameter 287 of second opening 288 may be directly measured using at least one of a probe, a gauge, a micrometer, or other desirable measuring device. Diameter 289 of second fastener 290 may be directly measured using a gauge, a micrometer, or other desirable measuring device. The difference between diameter 287 of second opening 288 and diameter 289 of second fastener 290 may be described as gap 291.

As standard 269 is a model to perform comparative evaluations, diameter 282 and diameter 287 may be intentionally different. For example, diameter 282 may be smaller than diameter 287. As a result, gap 286 would be smaller than gap 291. In some illustrative examples, number of openings 280 may be formed progressively larger moving across standard 269. As a result, a range of gaps would be formed in standard 269.

Further, other out of tolerance conditions may be intentionally formed in standard 269. For example, at least one of elongated openings, double drilled openings, or mis-selected fasteners may be present in standard 269.

Number of fasteners 281 may take the form of rivets 292 or bolts 293. In some illustrative examples, number of fasteners 281 may instead take the form of rods, bars, welding material, or any other type of fasteners. Number of fasteners 281 may take the same form as number of fasteners 222. For example, if number of fasteners 222 includes bolts 238, number of fasteners 281 includes bolts 293. By number of fasteners 222 and number of fasteners 281 being the same, the material of standard 269 and workpiece 206 may be substantially the same.

Standard 269 is inspected using x-ray inspection equipment 202. Results from inspection of standard 269 using x-ray inspection equipment 202 are used to generate standardized data 277. Data from inspection of standard 269 using x-ray inspection equipment 202 may be compared to the sizes of gaps between number of openings 280 and number of fasteners 281 which were determined from the direct measurements. For example, gray values of pixels in an image of standard 269 may be correlated with determined gaps using the directly measured diameters. Further, the sizes of the gaps determined from the direct measurements may be correlated to values on a plot profile of standard 269. Yet further, the sizes of gaps determined from the direct measurements may be correlated to data from inspection of standard 269 using x-ray inspection equipment 202 using equation 279. Equation 279 may be a relationship between the size of a gap and the background. For example, equation 279 may be a relationship between a ratio and an estimated gap size. The ratio may be a ratio of a difference over a background gray value. The difference may be a difference between the background gray value and a minimum gray value in a valley. In these illustrative examples, the ratio may be a ratio of a difference between a background gray value and a minimum gray value in a valley over the background gray value for standard 269.

Standardized data 277 from inspection of standard 269 may be used to determine if an out of tolerance condition exists in workpiece 206. For example, raw data image 257 may be compared to a raw data image of standard 269 in standardized data 277. As another example, lowest value 267 may be compared to limit 268 which may be formed from standardized data 277. As a further example, data from an analysis of plot profile 261 may be inputted into equation 279 of standardized data 277 and used to determine if an out of tolerance condition exists in workpiece 206.

Further, standardized data 277 may be used to determine estimated gap 294. Estimated gap 294 may be a value of a gap, such as gap 248, present in workpiece 206. By determining a value of a gap, the extent of an out of tolerance condition may be quantified.

Plot profile 261 may also be used to determine estimated gap 294. For example, lowest value 267 may be used to determine estimated gap 294. Lowest value 267 of valley 266 may be used to determine estimated gap 294. Difference 295 may be determined between lowest value 267 and a background value. The background value may be background 278 determined from standard 269 or background 265 determined from workpiece 206. Ratio 296 of difference 295 over the same background value may be determined.

Ratio 296 may be inputted into equation 279 to determine estimated gap 294. Estimated gap 294 may be a quantitative value. Estimated gap 294 may be an approximate size of a gap between a fastener and an opening in workpiece 206. Estimated gap 294 may be compared to a limit. Below the limit, estimated gap 294 may be a desirable value. Above the limit, estimated gap 294 may be an undesirable value. For example, above the limit, estimated gap 294 may be out of tolerance.

Difference 295 may be used to determine if an out of tolerance condition exists. For example, if difference 295 is above limit 297, an out of tolerance condition may exist.

Output 298 may be generated if an out of tolerance condition is determined. For example, output 298 may be generated if estimated gap 294 is out of tolerance. In some illustrative examples, output 298 may be generated if difference 295 is above limit 297. In some illustrative examples, output 298 may be generated if lowest value 267 is below limit 268. In some illustrative examples, output 298 may be generated based on direct review of at least one of raw data image 257 or image 258. Output 298 may take the form of an email, a text, an indicator light, an indicator message, an alarm, or other desirable output.

Figure 3:
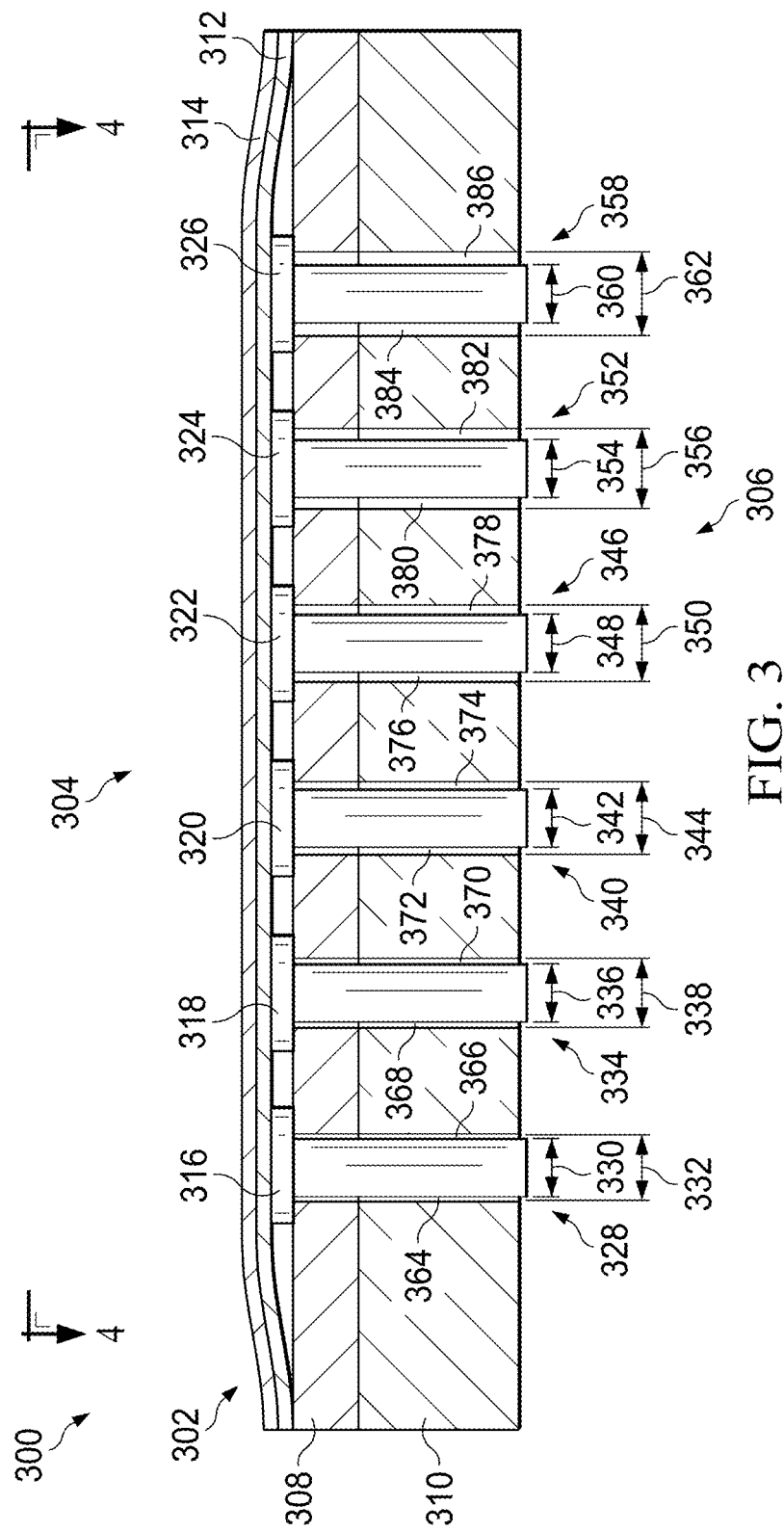
FIG. 3 is an illustration of a cross-sectional view of a standard in accordance with an illustrative embodiment.

Turning now to FIG. 3, an illustration of a cross-sectional view of a standard is depicted in accordance with an illustrative embodiment. Standard 300 may be an illustration of a physical implementation of standard 269 of FIG. 2. Standard 300 may be inspected using x-ray inspection equipment 202 of FIG. 2.

Standard 300 may be formed of substantially the same materials as workpiece 206 of FIG. 2. Standard 300 may be formed intentionally with a number of different sizes of openings. Thus, standard 300 may be formed with a number of different sizes of gaps. Standard 300 may be used to form standardized data for identification of gaps and quantification of sizes of gaps of a workpiece such as workpiece 206 of FIG. 2.

Standard 300 has number of objects 302 and number of fasteners 304. As depicted, number of fasteners 304 are installed in number of openings 306 through first object 308 and second object 310. Layer 312 and layer 314 may cover number of fasteners 304 and first object 308. In some illustrative examples, at least one of layer 312 or layer 314 may have stand-off or an air-gap between them. Layer 312 and layer 314 may be selected from any desirable material. In some illustrative examples, at least one of layer 312 or layer 314 may be selected from one of a paint, a surface coating, a metal, a composite material, or other material.

Number of fasteners 304 includes fastener 316, fastener 318, fastener 320, fastener 322, fastener 324, and fastener 326. Number of fasteners 304 may each be selected such that each of number of fasteners 304 has the same advertised dimensions. Fastener 316 extends through opening 328 of number of openings 306. Fastener 316 has diameter 330. To measure diameter 330 directly, layer 312, layer 314, and fastener 316 must first be removed. Then, diameter 330 may be directly measured using a gauge, a micrometer, or other desirable measuring device. Opening 328 has diameter 332. To measure diameter 332 directly, layer 312, layer 314, and fastener 316 must first be removed. As depicted, diameter 332 is greater than diameter 330. In some illustrative examples, fastener 316 and opening 328 may have an interference fit. In these illustrative examples, diameter 332 and diameter 330 may be substantially the same.

Fastener 318 extends through opening 334 of number of openings 306. Fastener 318 has diameter 336. Opening 334 has diameter 338. As depicted, diameter 338 is greater than diameter 332. To measure either diameter 336 or diameter 338 directly, layer 312, layer 314, and fastener 318 must first be removed. As depicted, diameter 330 and diameter 336 may be substantially the same. Also, diameter 338 is greater than diameter 336. As a result of diameter 338 being greater than diameter 332, the difference between diameter 336 and diameter 338 is greater than the difference between diameter 330 and diameter 332.

Fastener 320 extends through opening 340 of number of openings 306. Fastener 320 has diameter 342. Opening 340 has diameter 344. To measure either diameter 342 or diameter 344 directly, layer 312, layer 314, and fastener 320 must first be removed. As depicted, diameter 330 and diameter 342 may be substantially the same. Also, diameter 344 is greater than diameter 342. As a result of diameter 344 being greater than diameter 332, the difference between diameter 342 and diameter 344 is greater than the difference between diameter 330 and diameter 332.

Fastener 322 extends through opening 346 of number of openings 306. Fastener 322 has diameter 348. Opening 346 has diameter 350. To measure either diameter 348 or diameter 350 directly, layer 312, layer 314, and fastener 322 must first be removed. As depicted, diameter 330 and diameter 348 may be substantially the same. Also, diameter 350 is greater than diameter 348. As a result of diameter 350 being greater than diameter 332, the difference between diameter 348 and diameter 350 is greater than the difference between diameter 330 and diameter 332.

Fastener 324 extends through opening 352 of number of openings 306. Fastener 324 has diameter 354. Opening 352 has diameter 356. To measure either diameter 354 or diameter 356 directly, layer 312, layer 314, and fastener 324 must first be removed. As depicted, diameter 330 and diameter 354 may be substantially the same. Also, diameter 356 is greater than diameter 354. As a result of diameter 356 being greater than diameter 332, the difference between diameter 354 and diameter 356 is greater than the difference between diameter 330 and diameter 332.

Fastener 326 extends through opening 358 of number of openings 306. Fastener 326 has diameter 360. Opening 358 has diameter 362. To measure either diameter 360 or diameter 362 directly, layer 312, layer 314, and fastener 326 must first be removed. As depicted, diameter 330 and diameter 360 may be substantially the same. Also, diameter 362 is greater than diameter 360. As a result of diameter 362 being greater than diameter 332, the difference between diameter 360 and diameter 362 is greater than the difference between diameter 330 and diameter 332.

As depicted, each of number of fasteners 304 is substantially centered in each of number of openings 306. As diameters of number of openings 306 increase from opening 328 towards opening 358, the gaps between number of fasteners 304 and number of openings 306 increase moving from opening 328 to opening 358.

For example, gap 364 and 366 may be smaller than gap 368 and gap 370. Gap 364, gap 366, gap 368, gap 370, gap 372, and gap 374 may have acceptable sizes. For example, gap 374, gap 372, gap 370, gap 368, gap 366, and gap 364 may be considered within tolerance. Gap 376, gap 378, gap 380, gap 382, gap 384, and gap 386 may have unacceptable sizes. For example, gap 376, gap 378, gap 380, gap 382, gap 384, and gap 386 may be considered out of tolerance.

In some illustrative examples, the difference between the diameter of a fastener and the diameter of an opening may be considered rather than the gap between the fastener and the opening. For example, the difference between diameter 330 and diameter 332 may have an acceptable size. As another example, the difference between diameter 336 and diameter 338 may have an acceptable size. The difference between diameter 348 and diameter 350 may be considered out of tolerance. The difference between diameter 354 and diameter 356 may be considered out of tolerance. Likewise, the difference between diameter 360 and diameter 362 may be considered out of tolerance.

Turning now to FIG. 4, an illustration of a raw data image is depicted in accordance with an illustrative embodiment. Raw data image 400 may be formed based on the backscatter received by a detector system such as detector system 212 of FIG. 2. In some illustrative examples, raw data image 400 may be an image of data from an inspection of standard 300 of FIG. 3. In these illustrative examples, raw data image 400 may be a top view of standard 300 from direction 4 of FIG. 3. In this illustrative example, the diameters of number of fasteners 304 and number of openings 306 of FIG. 3 directly measured may be used to identify out of tolerance conditions. The identified out of tolerance conditions from the direct diameter measurements may then be used to identify how out of tolerance conditions may look in a raw data image such as raw data image 400. Thus, inspection of standard 300 may form standardized data such as standardized data 277 of FIG. 2.

Raw data image 400 includes background 402, number of fasteners 404, and number of openings 406. Number of fasteners 404 may be number of fasteners 304 of FIG. 3. Number of openings 406 may be number of openings 306 of FIG. 3. As can be seen in raw data image 400, a gap between a fastener in number of fasteners 404 and an opening in number of openings 406 may be indicated by a black ring. As can be seen in raw data image 400, as a difference between a diameter of a fastener in number of fasteners 404 and a diameter of an opening in number of openings 406 increases, the size of the black ring may increase. Further, as can be seen in raw data image 400, as a difference between a diameter of a fastener in number of fasteners 404 and a diameter of an opening in number of openings 406 increases, a darkness of the ring may increase from a gray to a nearly complete black. The darkness of a pixel in raw data image 400 may be directly related to the amount of backscatter received by a pixel of a detector system.

Number of fasteners 404 may include fastener 408, fastener 410, fastener 412, fastener 414, fastener 416, and fastener 418. Number of openings 406 may include opening 420, opening 422, opening 424, opening 426, opening 428, and opening 430.

A distinctive black ring is not present between fastener 408 and opening 420 in raw data image 400. Direct measurements of diameter 330 and diameter 332 of FIG. 3 may not show an out of tolerance condition. The characteristics of the shading between fastener 408 and opening 420 may be correlated with not having an out of tolerance condition. Upon viewing raw data image 400, an operator or computer system may determine that an out of tolerance gap is not present between fastener 408 and opening 420.

In one illustrative example, fastener 408 and opening 420 may be an interference fit. In this example, fastener 408 and opening 420 may have no gap between them. In this example, the gap may be about 0 inches.

Ring 432 may be seen between fastener 410 and opening 422. Direct measurements of diameter 336 and diameter 338 of FIG. 3 may not show an out of tolerance condition. The characteristics of ring 432 may be correlated with not having an out of tolerance condition. Ring 432 includes a number of shades of gray. Ring 432 does not appear black. Ring 432 may not indicate an out of tolerance gap. Upon viewing raw data image 400, an operator or computer system may determine that an out of tolerance gap is not present between fastener 410 and opening 422.

In one illustrative example, fastener 410 and opening 422 may not be an interference fit. In this example, fastener 410 and opening 422 may have a gap between them. In this example, the gap may be about 0.001 inches.

Ring 434 may be seen between fastener 412 and opening 424. As can be seen in raw data image 400, fastener 412 is not centered within opening 424. Direct measurements of diameter 342 and diameter 344 of FIG. 3 may not show an out of tolerance condition. The characteristics of ring 434 may be correlated with not having an out of tolerance condition. Ring 434 includes an apparently black crescent shape and a gray portion. Ring 434 may not indicate an out of tolerance gap. Upon viewing raw data image 400, an operator or computer system may determine that an out of tolerance gap is not present between fastener 412 and opening 424.

In one illustrative example, fastener 412 and opening 424 may not be an interference fit. In this example, fastener 412 and opening 424 may have a gap between them. In this example, the gap may be about 0.0025 inches.

Ring 436 may be seen between fastener 414 and opening 426. As can be seen in raw data image 400, fastener 414 is not centered within opening 426. Direct measurements of diameter 348 and diameter 350 of FIG. 3 may show an out of tolerance condition. The characteristics of ring 436 may be correlated with having an out of tolerance condition. Ring 436 has a majority of black or substantially black pixels. Ring 436 may indicate an out of tolerance gap. Upon viewing raw data image 400, an operator or computer system may determine that an out of tolerance gap is present between fastener 414 and opening 426.

In one illustrative example, fastener 414 and opening 426 may not be an interference fit. In this example, fastener 414 and opening 426 may have a gap between them. In this example, the gap may be about 0.0075 inches.

Ring 438 may be seen between fastener 416 and opening 428. Direct measurements of diameter 354 and diameter 356 of FIG. 3 may show an out of tolerance condition. The characteristics of ring 438 may be correlated with having an out of tolerance condition. Ring 438 has substantially the same thickness around fastener 416. Ring 438 appears to be entirely black or substantially black. Ring 438 may indicate an out of tolerance gap. Upon viewing raw data image 400, an operator or computer system may determine that an out of tolerance gap is present between fastener 416 and opening 428.

In one illustrative example, fastener 416 and opening 428 may not be an interference fit. In this example, fastener 416 and opening 428 may have a gap between them. In this example, the gap may be about 0.0125 inches.

Ring 440 may be seen between fastener 418 and opening 430. Direct measurements of diameter 344 and diameter 342 of FIG. 3 may show an out of tolerance condition. The characteristics of ring 440 may be correlated with having an out of tolerance condition. Ring 440 has substantially the same thickness around fastener 418. Ring 440 appears to be entirely black or substantially black. Ring 440 is thicker than ring 438. Thus, if ring 438 indicates an out of tolerance gap, ring 440 may also indicate an out of tolerance gap. Ring 440 may indicate an out of tolerance gap independent of the status of ring 438. Upon viewing raw data image 400, an operator or computer system may determine that an out of tolerance gap is present between fastener 418 and opening 430.

In one illustrative example, fastener 418 and opening 430 may not be an interference fit. In this example, fastener 418 and opening 430 may have a gap between them. In this example, the gap may be about 0.0225 inches.

Non-limiting illustrative examples of values of gaps between number of fasteners 404 and number of openings 406 were provided for illustrative purposes only. These illustrative examples are not meant to imply physical or architectural limitations to the manner in which an illustrative embodiment may be implemented.

Turning now to FIG. 5, an illustration of an image is depicted in accordance with an illustrative embodiment. Image 500 may be a physical implementation of image 258 of FIG. 2. Image 500 may be an image resulting from performing a filter, such as filter 260 of FIG. 2, on raw data image 400 of FIG. 4. In some illustrative examples, image 500 may be an image resulting from performing a bandpass filter on raw data image 400 of FIG. 4.

An out of tolerance condition may be identified directly from image 500. For example, image 500 may be observed by a human operator to determine if an out of tolerance condition is present. In some illustrative examples, observation by a human operator may be a first step in determining if an out of tolerance condition is present. Image 500 may be analyzed by a computer system. In some illustrative examples, analysis by computer system may be a first step in determining if an out of tolerance condition is present.

In other illustrative examples, image 500 may be indirectly used to determine if an out of tolerance condition is present. For example, data may be taken from image 500. This data may then be processed. The processed data may be used to determine if an out of tolerance condition is present.

For example, grayscale values from line 502 may be extracted. A plot profile of the grayscale values of line 502 may be formed. This plot profile may then be analyzed to determine if an out of tolerance condition exists. In some illustrative examples, data taken from the plot profile may be used to determine if an out of tolerance condition exists.

In some illustrative examples, gray values may be taken from several locations in each fastener. For example, gray values may be taken from line 504 and line 506 to create additional plot profiles that may be analyzed. By sampling from multiple lines through a fastener in a workpiece, an out of tolerance gap may be determined even if the fastener is not centered. Although three lines, line 502, line 504, and line 506 are shown with a single fastener, any desirable number of lines may be sampled. For example, two lines of gray values may be sampled from a fastener in an image. In another example, more than three lines of gray values may be sampled from a fastener in an image.

Figure 6:
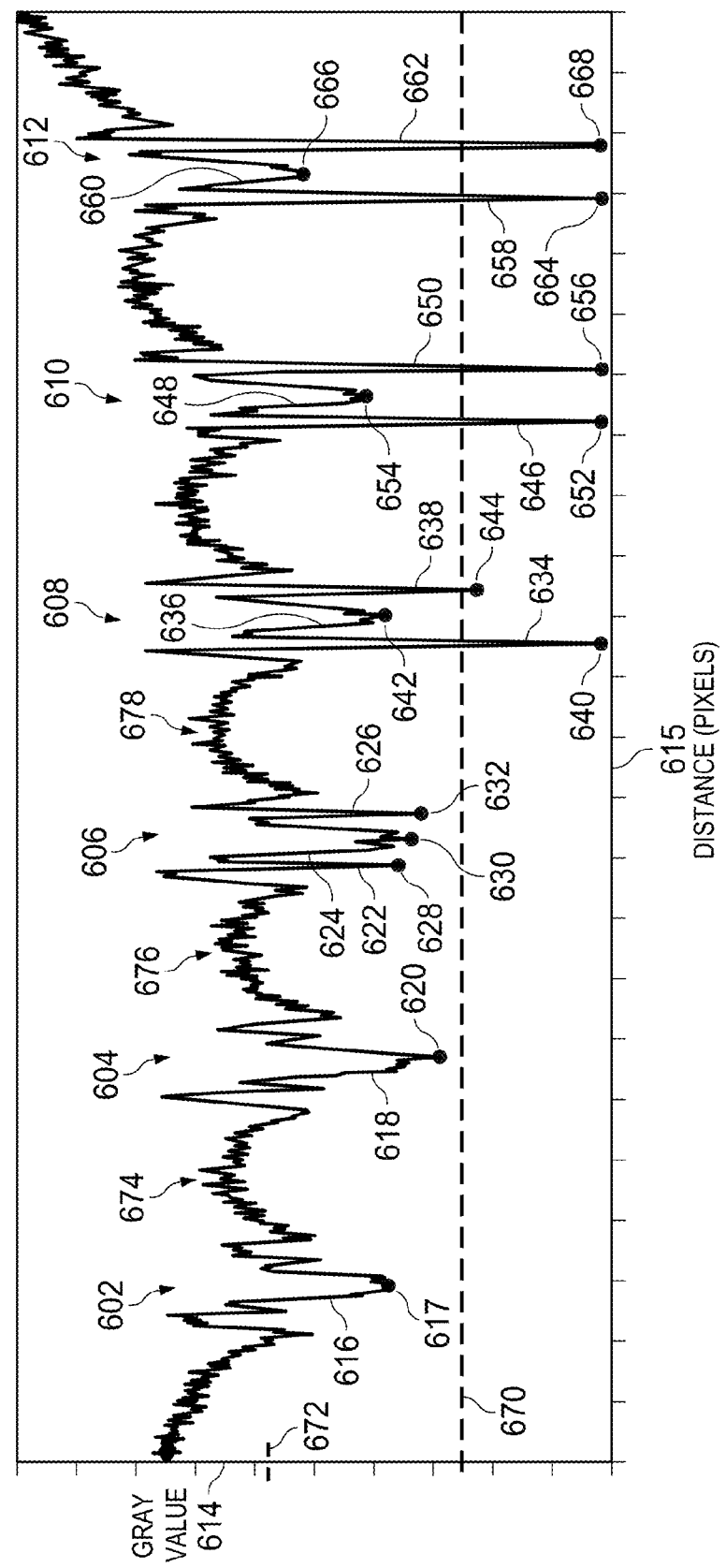
FIG. 6 is an illustration of a plot profile in accordance with an illustrative embodiment.

Turning now to FIG. 6, an illustration of a plot profile is depicted in accordance with an illustrative embodiment. Plot profile 600 may be a plot profile of data from image 500 of FIG. 5. For example, plot profile 600 may be a plot profile of data from line 502 of FIG. 5.

Plot profile 600 may be used in conjunction with identified out of tolerance conditions for standard 300 of FIG. 3 to form standardized data. For example, plot profile 600 may be used with diameters of number of fasteners 304 and number of openings 306 of FIG. 3 from direct measurements to identify out of tolerance conditions on plot profile 600.

Area 602 may correspond to a plot profile of fastener 408 and opening 420. Area 604 may correspond to a plot profile of fastener 410 and opening 422. Area 606 may correspond to a plot profile of fastener 412 and opening 424. Area 608 may correspond to a plot profile of fastener 414 and opening 426. Area 610 may correspond to a plot profile of fastener 416 and opening 428. Area 612 may correspond to a plot profile of fastener 418 and opening 430.

Plot profile 600 may be a plot of gray value 614 over distance 615. Distance 615 may be measured in pixels. A lower gray value along gray value 614 correlates to a darker pixel. A higher gray value along gray value 614 correlates to a lighter pixel. Distance 615 may increase in direction 6 of FIG. 5 along line 502.

As can be seen in plot profile 600, area 602 includes valley 616. Valley 616 has lowest point 617. Area 604 has valley 618. Valley 618 has lowest point 620. Area 606 has valley 622, valley 624, and valley 626. Valley 622 has lowest point 628. Valley 624 has lowest point 630. Valley 626 has lowest point 632. Area 608 has valley 634, valley 636, and valley 638. Valley 634 has lowest point 640. Valley 636 has lowest point 642. Valley 638 has lowest point 644. Area 610 has valley 646, valley 648, and valley 650. Valley 646 has lowest point 652. Valley 648 has lowest point 654. Valley 650 has lowest point 656. Area 612 has valley 658, valley 660, and valley 662. Valley 658 has lowest point 664. Valley 660 has lowest point 666. Valley 662 has lowest point 668.

Valley 616, valley 618, valley 624, valley 636, valley 648, and valley 660 may correspond to gray values from number of fasteners 404 of FIG. 4. Valley 622, valley 626, valley 634, valley 638, valley 646, valley 650, valley 658, and valley 662 may correspond to gray values from spaces between number of fasteners 404 and number of openings 406 of FIG. 4.

Area 602, area 604, and area 606 may represent fasteners that do not have any out of tolerance conditions. For example, diameters of number of fasteners 304 and number of openings 306 from direct measurements may show the fasteners and openings represented by area 602, area 604, and area 606 may not have out of tolerance conditions. Area 608, area 610, and area 612 may represent fasteners that have out of tolerance conditions. For example, diameters of number of fasteners 304 and number of openings 306 from direct measurements may show the fasteners and openings represented by area 608, area 610, and area 612 may each have out of tolerance conditions. By contrasting area 602, area 604, and area 606 with area 608, area 610, and area 612, limit 670 may be set. Limit 670 may be set such that lowest point 617, lowest point 620, lowest point 628, lowest point 630, lowest point 632, lowest point 642, lowest point 654, and lowest point 666 are above limit 670. Limit 670 may be set such that a desirable percentage of at least one of true positives, true negatives, false negatives, or false positives may occur. The true positive rate may also be called sensitivity. The true negative rate may also be called specificity.

If a value falls below limit 670, it may indicate an out of tolerance condition. If a value falls below limit 670, an output may be generated. The output may be an indication for additional review or additional inspection.

An out of tolerance gap was measured in relation to fastener 322, fastener 324, and fastener 326 of FIG. 3. As can be seen in plot profile 600, each of lowest point 640, lowest point 644, lowest point 652, lowest point 656, lowest point 664, and lowest point 668 which is associated with fastener 322, fastener 324, and fastener 326, fall below limit 670.

Limit 670 may be an example of standardized data. Another example of standardized data may be background 672. Background 672 may be a value selected to be an average value for gray value 614 in areas which do not have number of openings 406 of FIG. 4. For example, background 672 may be an average value for background area 674, background area 676, and background area 678. Background 672 may be used to determine if an out of tolerance condition exists. For example, a difference between background 672 and a lowest point of a valley may be determined. If the difference is above a limit, an out of tolerance condition may exist. Further, background 672 may be used in calculations to determine a relative size of a gap.

In some illustrative examples, out of tolerance conditions may be determined from a plot profile by identifying lowest points of valleys that fall below a preset limit. For example, a workpiece may be inspected. The workpiece may have substantially the same material layup as standard 300 of FIG. 3. Data from the inspection may be used to form an image and a plot profile may be formed using that image. Lowest points in valleys of that plot profile may be compared to limit 670 from FIG. 6. This process may be used to identify potentially out of tolerance conditions.

Figure 7:
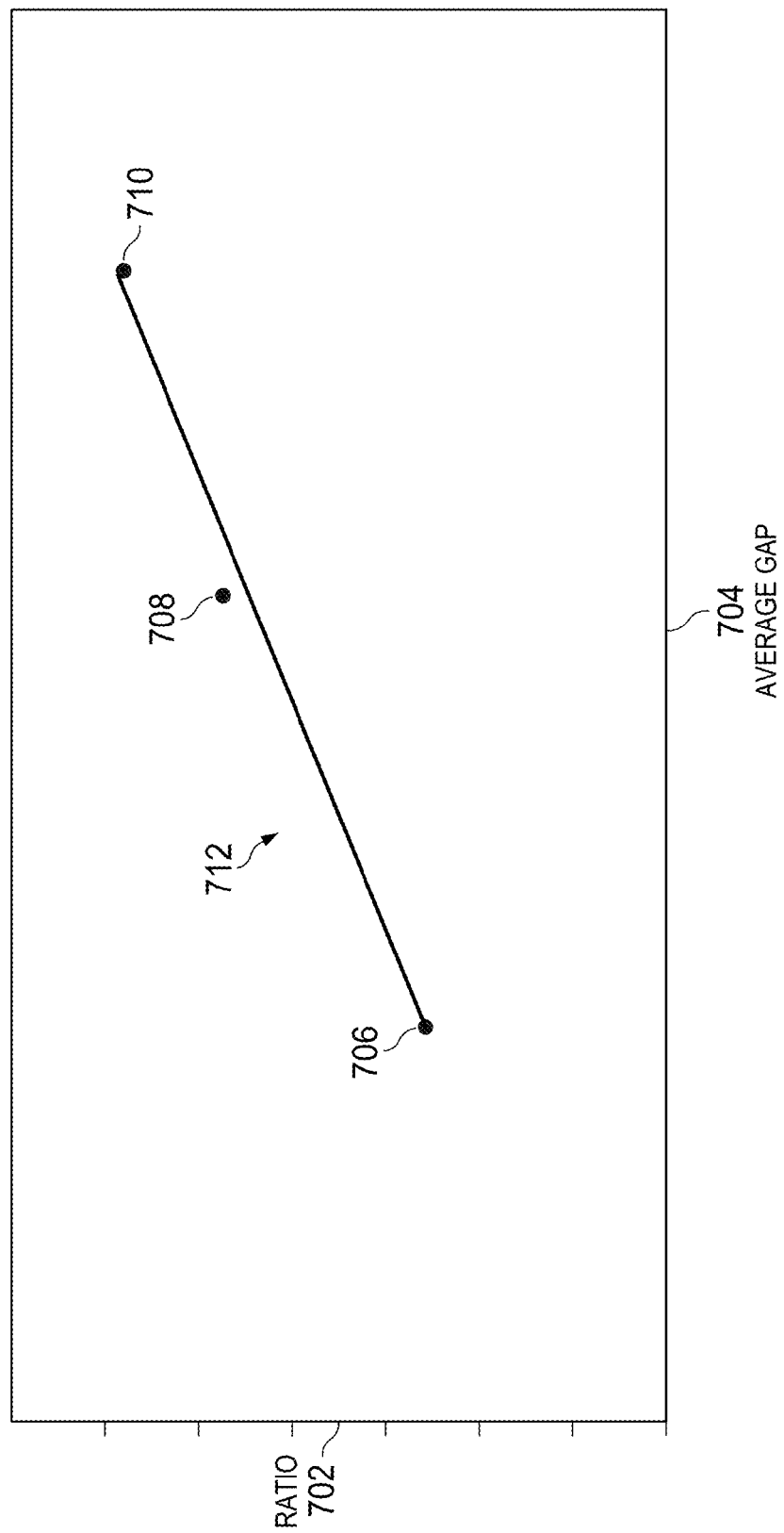
FIG. 7 is an illustration of a ratio equation in accordance with an illustrative embodiment.

Turning now to FIG. 7, an illustration of a ratio equation is depicted in accordance with an illustrative embodiment. Ratio plot 700 may be a form of standardized data 277 of FIG. 2. Ratio plot 700 may be formed using data from plot profile 600 of FIG. 6. Ratio plot 700 may include ratio 702 versus average gap 704. Ratio 702 may be determined by first determining a difference between a background and a lowest point in a valley and then determining a ratio of the difference over the background. For example, a ratio may be the difference between background 672 and lowest point 640 over background 672 of FIG. 6.

Ratios for several lowest values in a plot profile may be plotted. Ratio plot 700 includes point 706, point 708, and point 710. Ratio equation 712 may be determined by fitting a straight line to point 706, point 708, and point 710. Ratio equation 712 may provide an approximate gap size for a given ratio value. Ratio equation 712 may be equation 279 of FIG. 2.

Ratio equation 712 may be used to determine approximate gaps between fasteners and openings in a workpiece. For example, ratio equation 712 may be used to determine approximate gaps between number of fasteners 222 and number of openings 224 of workpiece 206 of FIG. 2.

In order to use ratio equation 712, a ratio must be determined for a lowest point of a valley in a plot profile for the workpiece. The ratio is a ratio of a difference between a background and the lowest point over the background. The background may be background 672 of FIG. 6 or a background determined from the plot profile of the workpiece. The determined ratio may be input into ratio equation 712 to determine an estimated gap. If the estimated gap is larger than a predetermined limit, an out of tolerance condition may exist.

Figure 8:
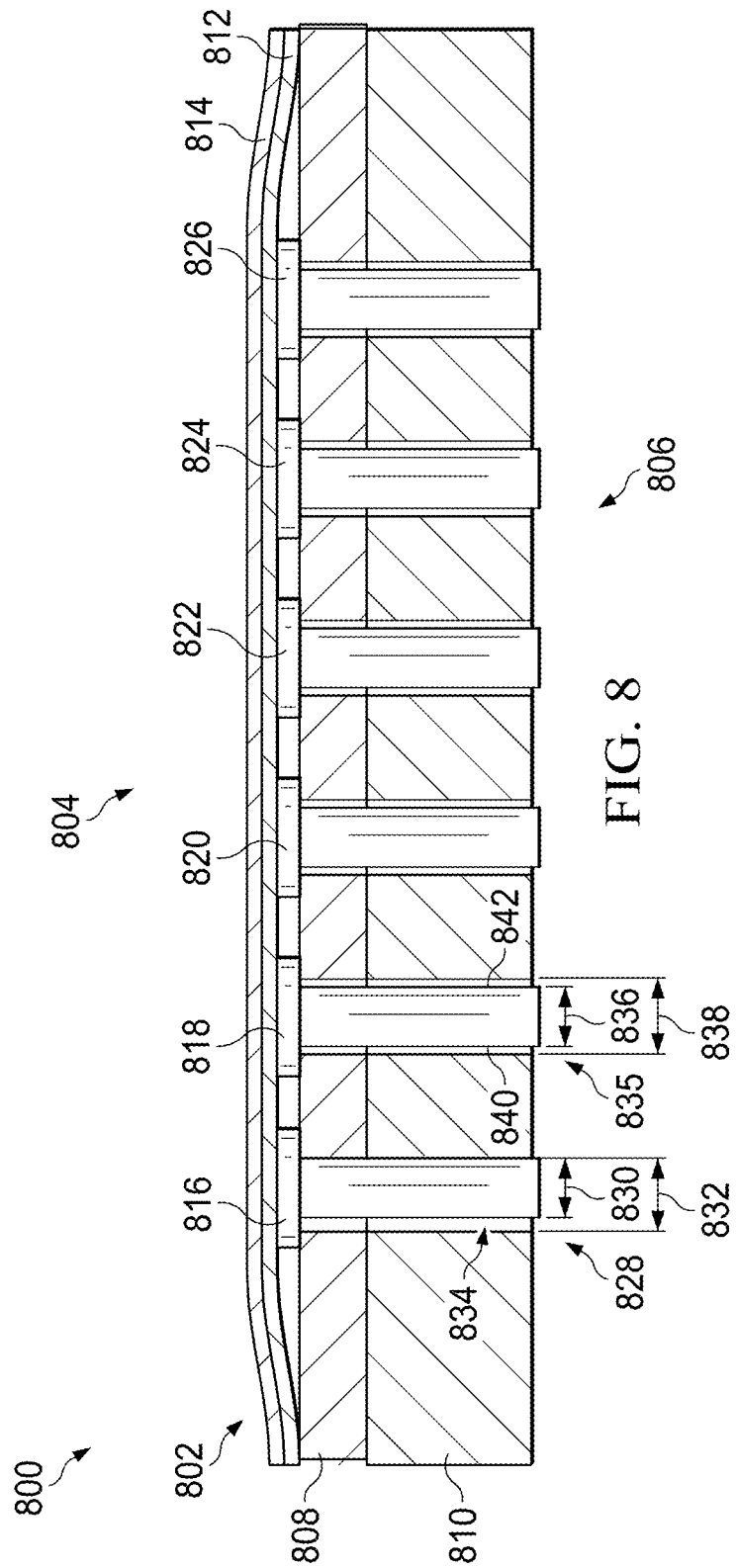
FIG. 8 is an illustration of a cross-sectional view of a workpiece in accordance with an illustrative embodiment.

Turning now to FIG. 8, an illustration of a cross-sectional view of a workpiece is depicted in accordance with an illustrative embodiment. Workpiece 800 may be an illustration of a physical implementation of workpiece 206 of FIG. 2. Workpiece 800 may be inspected for any out of tolerance gaps. Workpiece 800 may be inspected using x-ray inspection equipment 202 of FIG. 2.

Workpiece 800 has number of objects 802 and number of fasteners 804. As depicted, number of fasteners 804 are installed in number of openings 806 through first object 808 and second object 810. Number of fasteners 804 may be desirably substantially the same size. For example, number of fasteners 804 may desirably each have substantially the same diameter. As another example, number of fasteners 804 may desirably each have substantially the same length. Thus, number of fasteners 804 may have the same advertised price from a manufacturer. However, manufacturing of number of fasteners 804 may have a tolerance that results in some amount of variation in the actual sizes of number of fasteners 804.

Layer 812 and layer 814 may cover number of fasteners 804 and first object 808. Layer 812 and layer 814 may be selected from any desirable material. In some illustrative examples, at least one of layer 812 or layer 814 may be selected from one of a paint, a surface coating, a metal, a composite material, or other material. In some illustrative examples, layer 812 and layer 814 may have an air gap between first object 808 and layer 812. In some illustrative examples, layer 812 may contact first object 808 in between each of number of fasteners 804.

Number of fasteners 804 includes fastener 816, fastener 818, fastener 820, fastener 822, fastener 824, and fastener 826. Fastener 816 extends through opening 828 of number of openings 806. Fastener 816 has diameter 830. To measure diameter 830 directly, layer 812, layer 814, and fastener 816 must first be removed. Then diameter 830 may be directly measured using a gauge, a micrometer, or other desirable measuring device. Opening 828 has diameter 832. To measure diameter 832 directly, layer 812, layer 814, and fastener 816 must first be removed.

As depicted, diameter 832 is greater than diameter 830. As depicted, gap 834 is present between fastener 816 and opening 828. As depicted, fastener 816 is not centered within opening 828. As a result, gap 834 may be larger than desired. For example, because fastener 816 is not centered within opening 828, gap 834 may be out of tolerance.

Fastener 818 extends through opening 835 of number of openings 806. Fastener 818 has diameter 836. To measure diameter 836 directly, layer 812, layer 814, and fastener 818 must first be removed. Then diameter 836 may be directly measured using a gauge, a micrometer, or other desirable measuring device. Opening 835 has diameter 838. To measure diameter 838 directly, layer 812, layer 814, and fastener 818 must first be removed.

As depicted, gap 840 and gap 842 may be present between fastener 818 and opening 835. Fastener 818 may be positioned substantially centered within opening 835. Thus, gap 840 and gap 842 may be substantially the same size. Gap 840 and gap 842 may have acceptable sizes.

Figure 9:
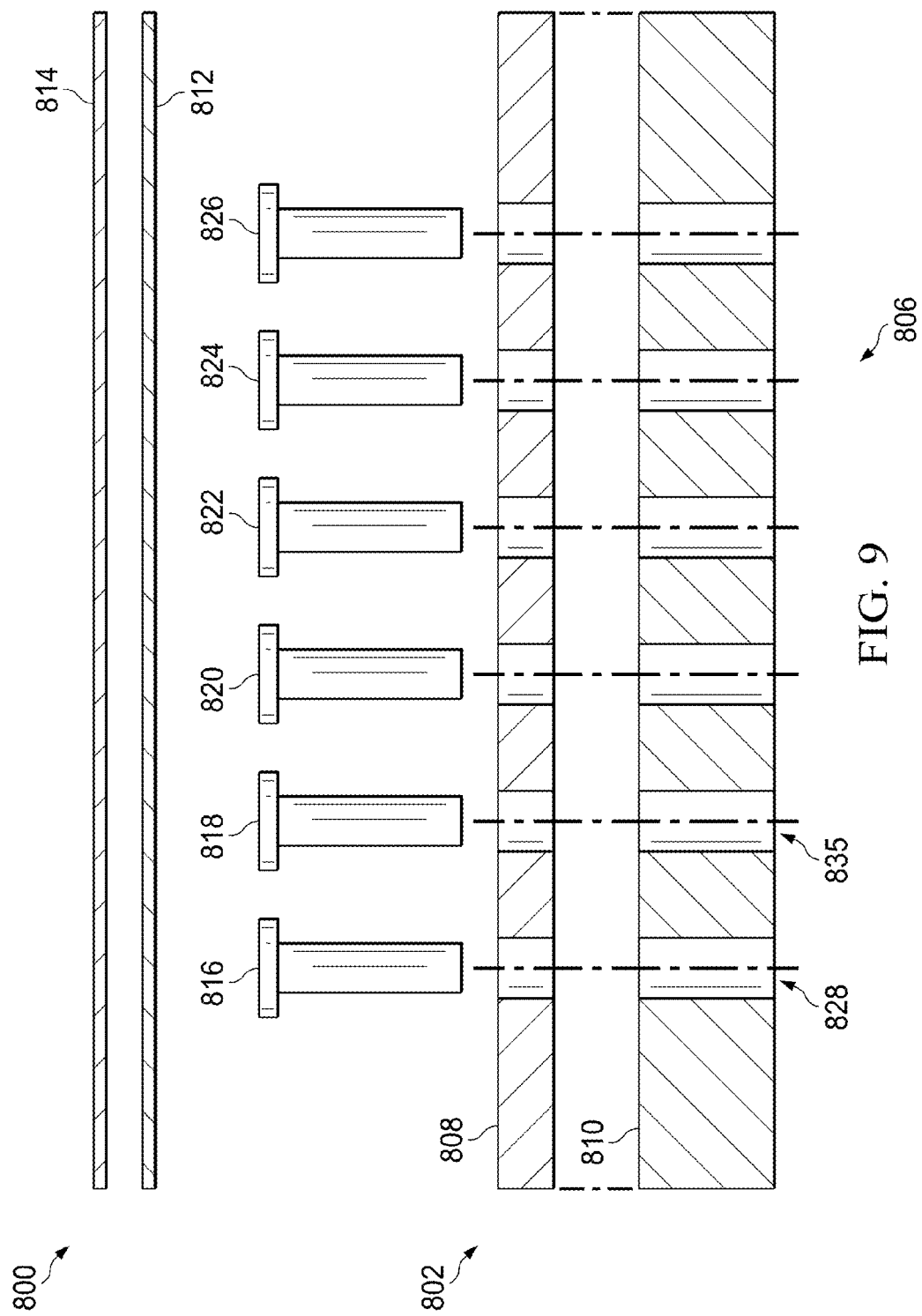
FIG. 9 is an illustration of an exploded cross-sectional view of a workpiece in accordance with an illustrative embodiment.

Turning now to FIG. 9, an illustration of an exploded cross-sectional view of a workpiece is depicted in accordance with an illustrative embodiment. In some illustrative examples, number of openings 806 may be counter sunk.

Figure 10:
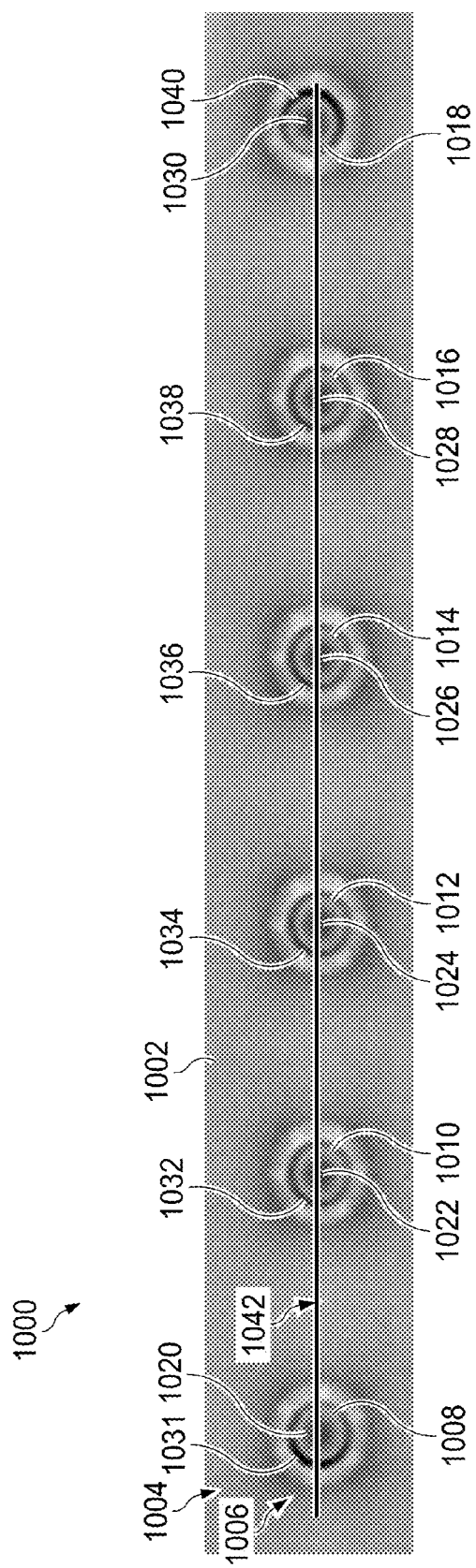
FIG. 10 is an illustration of a raw data image in accordance with an illustrative embodiment.

Turning now to FIG. 10, an illustration of a raw data image is depicted in accordance with an illustrative embodiment. In this illustrative example, raw data image 1000 may be an image of workpiece 800 of FIG. 8. In some illustrative examples, raw data image 1000 may be an illustration of raw data image 257 of FIG. 2. Raw data image 1000 may be created from data 208 and contrast adjustment 259 of FIG. 2.

Raw data image 1000 may be used to determine if an out of tolerance condition exists in workpiece 800 of FIG. 8. Raw data image 1000 may be used directly or indirectly to determine if an out of tolerance condition exists in workpiece 800. For example, raw data image 1000 may be directly analyzed to determine if an out of tolerance condition exists in workpiece 800. This may be a qualitative determination.

Raw data image 1000 may be directly observed by a human operator to determine if an out of tolerance condition is present. The human operator may determine if an out of tolerance condition is present for a single fastener and opening. The human operator may determine whether an undesirable number of out of tolerance conditions exist. Further, the human operator may determine whether a number of out of tolerance conditions are undesirable. Further, the human operator may determine whether the number of out of tolerance conditions is serious. For example, the human operator may determine if the workpiece should be reworked or scrapped. For example, a human operator may perform an analysis based on the basis for the out of tolerance condition. As an example, a fastener contacting one side of an opening may be less desirable than the fastener contacting the other side of the opening. As another example, a double drilled opening may be less desirable than an oversized opening.

To analyze raw data image 1000, the human operator may perform an analysis based on the specifications of workpiece. For example, the human operator may take into account the expected loads on the workpiece.

In some illustrative examples, observation by a human operator may be a first step in determining if an out of tolerance condition is present. For example, if a human operator determines an out of tolerance condition may be present, further processing may be performed to determine at least one of if an out of tolerance condition is present or the severity of the out of tolerance condition. Further processing may include direct analysis by a computer system, forming a plot profile, creating a ratio, plotting the ratio on a ratio to estimated gap size plot, or other desirable processing.

Raw data image 1000 may be directly analyzed by a computer system. In some illustrative examples, analysis by a computer system may be a first step in determining if an out of tolerance condition is present.

Analysis of raw data image 1000 may be performed by the computer system. The computer system may determine if an out of tolerance condition is present for a single fastener and opening. The computer system may determine whether an undesirable number of out of tolerance conditions exist. Further, the computer system may determine whether a number of out of tolerance conditions are undesirable. Further, the human operator may determine if the number of out of tolerance conditions is serious. For example, the computer system may determine if the workpiece should be reworked or scrapped. For example, the computer system may perform an analysis based on the basis for the out of tolerance condition. As an example, a fastener contacting one side of an opening may be less desirable than the fastener contacting the other side of the opening. As another example, a double drilled opening may be less desirable than an oversized opening.

To analyze raw data image 1000, the computer system may be programmed based on the specifications of the workpiece. For example, the computer system may be programmed based on the expected loads on the workpiece.

Raw data image 1000 includes background 1002, number of fasteners 1004, and number of openings 1006. Number of fasteners 1004 may be number of fasteners 804 of FIG. 8. Number of openings 1006 may be number of openings 806 of FIG. 8. As can be seen in raw data image 1000, a gap between a fastener in number of fasteners 1004 and an opening in number of openings 1006 may be indicated by a black ring. As can be seen in raw data image 1000, as a difference between a diameter of a fastener in number of fasteners 1004 and a diameter of an opening in number of openings 1006 increases, the size of the black ring may increase. Further, as can be seen in raw data image 1000, as a difference between a diameter of a fastener in number of fasteners 1004 and a diameter of an opening in number of openings 1006 increases, a darkness of the ring may increase from a gray to a nearly complete black. The darkness of a pixel in raw data image 1000 may be directly related to the amount of backscatter received by a pixel of a detector system.

Number of fasteners 1004 may include fastener 1008, fastener 1010, fastener 1012, fastener 1014, fastener 1016, and fastener 1018. Number of openings 1006 may include opening 1020, opening 1022, opening 1024, opening 1026, opening 1028, and opening 1030.

Ring 1031 may be seen between fastener 1008 and opening 1020. As can be seen in raw data image 1000, fastener 1008 is not centered within opening 1020. In some illustrative examples, direct measurements of diameter 830 and diameter 832 of FIG. 8 may not show an out of tolerance condition. However, due to the position of fastener 1008 within opening 1020, an out of tolerance condition may exist. In some illustrative examples, direct measurements of diameter 830 and diameter 832 of FIG. 8 may show an out of tolerance condition. However, due to the position of fastener 1008 within opening 1020, a greater out of tolerance condition may exist than indicated by the direct measurements. As a result, by determining an out of tolerance condition based on raw data image 1000, an out of tolerance condition may be determined based on loading conditions of the workpiece, operating standards of the workpiece, or other conditions of the assembled workpiece.

Ring 1031 includes an apparently black crescent shape and a gray portion. In some illustrative examples, an operator or image processing software may compare ring 1031 to standardized data, such as an image of a standard having known gap sizes. In this illustrative example, ring 1031 may be compared to raw data image 400 of FIG. 4. Ring 1031 substantially resembles ring 434 of raw data image 400 in FIG. 4. Accordingly, if ring 434 is classified as an out of tolerance gap, ring 1031 may also be an out of tolerance gap. However, if ring 434 of raw data image 400 is classified as not having an out of tolerance gap, ring 1031 may not be found to have an out of tolerance gap.

In some illustrative examples, ring 1031 may not indicate an out of tolerance gap. In these illustrative examples, upon viewing raw data image 1000, an operator or computer system may determine that an out of tolerance gap is not present between fastener 816 and opening 828. In some illustrative examples, ring 1031 may indicate an out of tolerance gap. In these illustrative examples, upon viewing raw data image 1000, an operator or computer system may determine that an out of tolerance gap may be present between fastener 816 and opening 828. In response to determining an out of tolerance gap may be present, additional analysis may be performed. For example, the size of a gap between fastener 816 and opening 828 may be quantified. In another example, a plot profile may be formed to determine if a lowest point in a valley is below a pre-selected limit.

Ring 1032 may be seen between fastener 1010 and opening 1022. Ring 1032 may be directly visually inspected for the darkness of ring 1032. Ring 1032 includes a number of shades of gray. Ring 1032 does not appear black. Accordingly, ring 1032 may not indicate an out of tolerance gap. Upon viewing raw data image 400, an operator or computer system may determine that an out of tolerance gap is not present between fastener 1010 and opening 1022.

In some illustrative examples, ring 1032 may be compared to standardized data, such as raw data image 400 of FIG. 4. Ring 1032 substantially resembles ring 432 of raw data image 400 in FIG. 4. Ring 432 is classified as not having an out of tolerance gap. Accordingly, ring 1032 also does not have an out of tolerance gap.

Ring 1034, ring 1036, and ring 1038 each include a number of shades of gray. Each of ring 1034, ring 1036, and ring 1038 appears substantially similar. None of ring 1034, ring 1036, or ring 1038 appears black. Accordingly, none of ring 1034, ring 1036, or ring 1038 may indicate an out of tolerance gap.

In some illustrative examples, each of ring 1034, ring 1036, and ring 1038 may be compared to standardized data, such as raw data image 400 of FIG. 4. Each of ring 1034, ring 1036, and ring 1038 substantially resembles ring 432 of raw data image 400 in FIG. 4. Ring 432 is classified as not having an out of tolerance gap. Accordingly, each of ring 1034, ring 1036, and ring 1038 also does not have an out of tolerance gap.

Ring 1040 may be seen between fastener 1018 and opening 1030. As can be seen in raw data image 1000, fastener 1018 is not centered within opening 1030. Due to the position of fastener 1018 within opening 1030, an out of tolerance condition may exist.

Ring 1040 includes an apparently black crescent shape and a gray portion. In some illustrative examples, an operator or image processing software may compare ring 1040 to standardized data, such as an image of a standard having known gap sizes. In this illustrative example, ring 1040 may be compared to raw data image 400 of FIG. 4. Ring 1040 substantially resembles a rotation of ring 434 of raw data image 400 in FIG. 4. Accordingly, if ring 434 is classified as an out of tolerance gap, ring 1040 may also be an out of tolerance gap. However, if ring 434 of raw data image 400 is classified as not having an out of tolerance gap, ring 1040 may not be found to have an out of tolerance gap.

After reviewing each of ring 1031, ring 1032, ring 1034, ring 1036, ring 1038, and ring 1040 individually, raw data image 1000 may be considered as a whole. For example, an out of tolerance condition for ring 1031 may be acceptable for qualifying workpiece 800. However, in some examples, having an out of tolerance condition for two or more of number of fasteners 1004 may not be acceptable to qualify workpiece 800. In some other examples, a single type of out of tolerance condition may be acceptable while another type of out of tolerance condition may not be acceptable. For example, a double drilled opening in number of openings 1006 may not be acceptable while a nominal gap formed by a fastener centered in an opening may be acceptable.

A plot profile may be formed based on raw data image 1000. For example, a plot profile may be formed of data within line 1042 of FIG. 10. In another example, a plot profile may be formed of data from a filtered image based on raw data image 1000. Lowest points in the plot profile formed based on raw data image 1000 may be compared to a limit, such as limit 670 of FIG. 6, to determine if an out of tolerance condition exists. This may be a qualitative determination. When a plot profile based on raw data image 1000 is used, raw data image 1000 may be used indirectly to determine an out of tolerance condition.

Further, an estimated gap may be determined from a ratio calculated from data of a plot profile. The estimated gap may be used to determine whether an out of tolerance condition exists. When an estimated gap is determined, this may be a quantitative determination of an out of tolerance gap. When an estimated gap is determined using a plot profile based on raw data image 1000, raw data image 1000 may be used indirectly to determine an out of tolerance condition.

Figure 11:
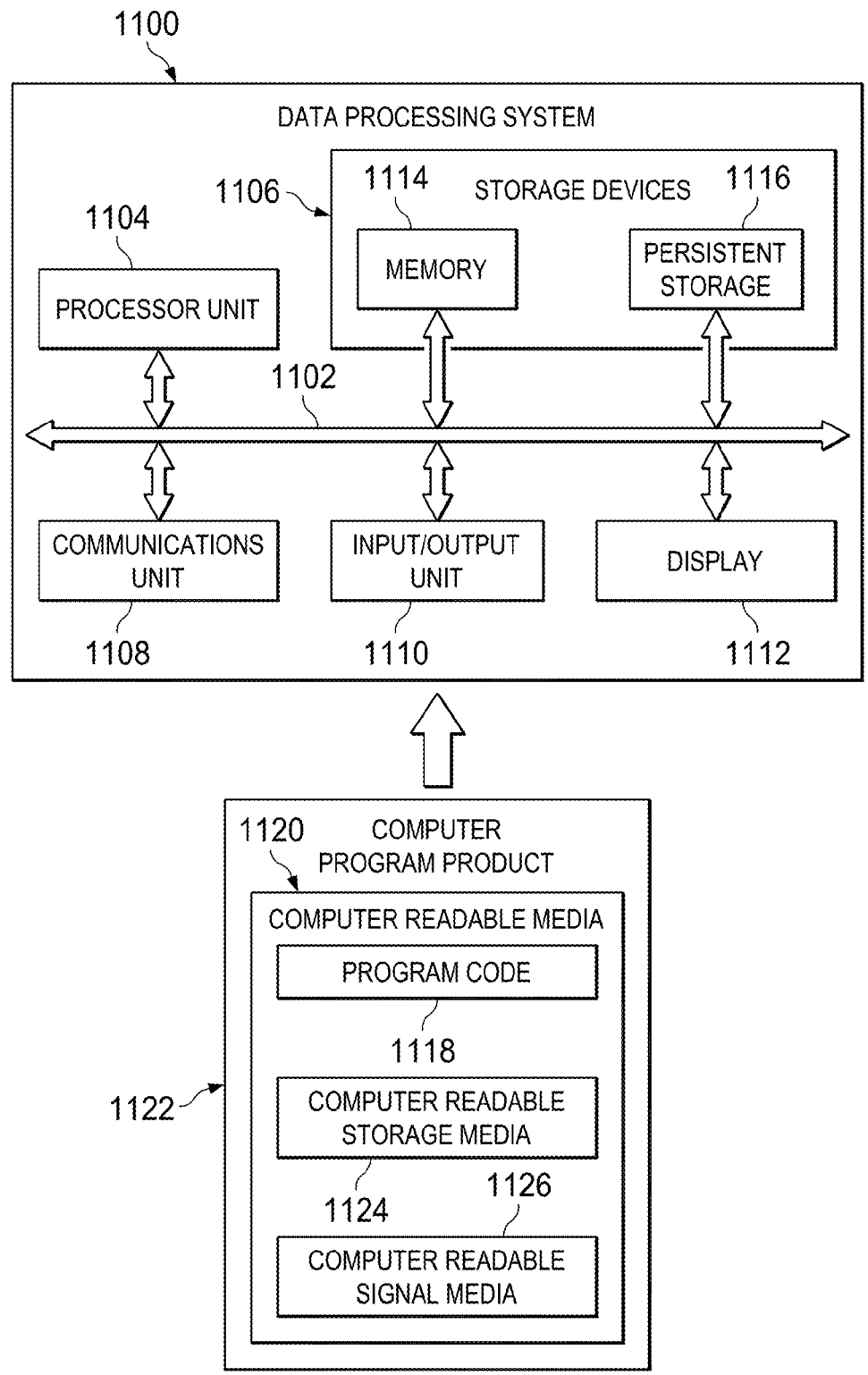
FIG. 11 is an illustration of a data processing system in the form of a block diagram in accordance with an illustrative embodiment.

Turning now to FIG. 11, an illustration of a data processing system in the form of a block diagram is depicted in accordance with an illustrative embodiment. Data processing system 1100 may be used to implement computers in computer system 204 of FIG. 2. As depicted, data processing system 1100 includes communications framework 1102, which provides communications between processor unit 1104, storage devices 1106, communications unit 1108, input/output unit 1110, and display 1112. In some cases, communications framework 1102 may be implemented as a bus system.

Processor unit 1104 is configured to execute instructions for software to perform a number of operations. Processor unit 1104 may comprise a number of processors, a multi-processor core, and/or some other type of processor, depending on the implementation. In some cases, processor unit 1104 may take the form of a hardware unit, such as a circuit system, an application-specific integrated circuit (ASIC), a programmable logic device, or some other suitable type of hardware unit.

Instructions for the operating system, applications, and/or programs run by processor unit 1104 may be located in storage devices 1106. Storage devices 1106 may be in communication with processor unit 1104 through communications framework 1102. As used herein, a storage device, also referred to as a computer readable storage device, is any piece of hardware capable of storing information on a temporary and/or permanent basis. This information may include, but is not limited to, data, program code, and/or other information.

Memory 1114 and persistent storage 1116 are examples of storage devices 1106. Memory 1114 may take the form of, for example, a random access memory or some type of volatile or non-volatile storage device. Persistent storage 1116 may comprise any number of components or devices. For example, persistent storage 1116 may comprise a hard drive, a flash memory, a rewritable optical disk, a rewritable magnetic tape, or some combination of the above. The media used by persistent storage 1116 may or may not be removable.

Communications unit 1108 allows data processing system 1100 to communicate with other data processing systems and/or devices. Communications unit 1108 may provide communications using physical and/or wireless communications links.

Input/output unit 1110 allows input to be received from and output to be sent to other devices connected to data processing system 1100. For example, input/output unit 1110 may allow user input to be received through a keyboard, a mouse, and/or some other type of input device. As another example, input/output unit 1110 may allow output to be sent to a printer connected to data processing system 1100.

Display 1112 is configured to display information to a user. Display 1112 may comprise, for example, without limitation, a monitor, a touch screen, a laser display, a holographic display, a virtual display device, and/or some other type of display device.

In this illustrative example, the processes of the different illustrative embodiments may be performed by processor unit 1104 using computer-implemented instructions. These instructions may be referred to as program code, computer usable program code, or computer readable program code and may be read and executed by one or more processors in processor unit 1104.

In these examples, program code 1118 is located in a functional form on computer readable media 1120, which is selectively removable, and may be loaded onto or transferred to data processing system 1100 for execution by processor unit 1104. Program code 1118 and computer readable media 1120 together form computer program product 1122. In this illustrative example, computer readable media 1120 may be computer readable storage media 1124 or computer readable signal media 1126.

Computer readable storage media 1124 is a physical or tangible storage device used to store program code 1118 rather than a medium that propagates or transmits program code 1118. Computer readable storage media 1124 may be, for example, without limitation, an optical or magnetic disk or a persistent storage device that is connected to data processing system 1100.

Alternatively, program code 1118 may be transferred to data processing system 1100 using computer readable signal media 1126. Computer readable signal media 1126 may be, for example, a propagated data signal containing program code 1118. This data signal may be an electromagnetic signal, an optical signal, and/or some other type of signal that can be transmitted over physical and/or wireless communications links. In some illustrative examples, functions have been described as being performed by a computer system. Although the term computer system is used, it should be understood that the function or functions may be performed by any appropriate component of data processing system 1100. For example, a function or functions may be performed by processor unit 1104.

Figure 12:
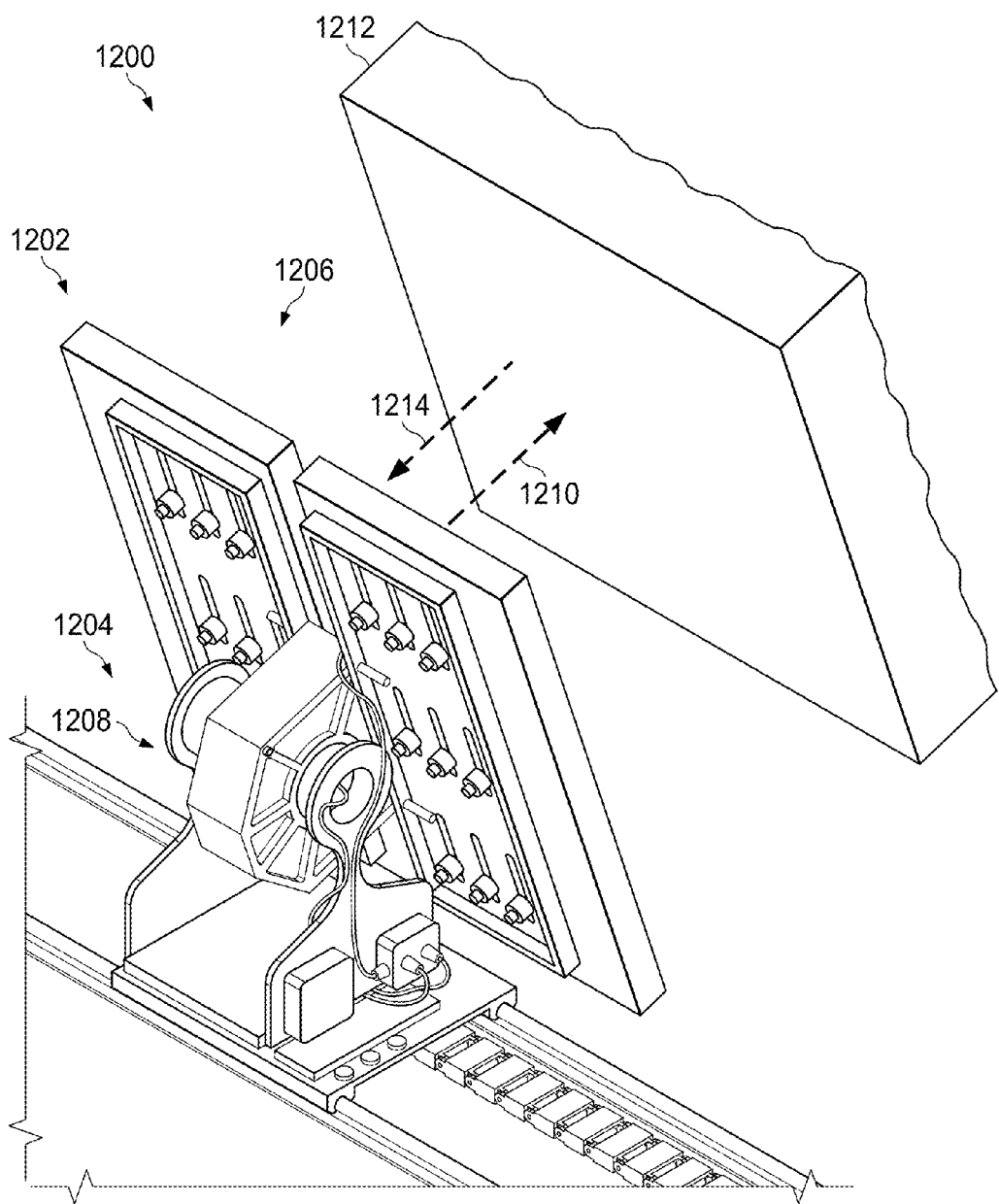
FIG. 12 is an illustration of an inspection environment in accordance with an illustrative embodiment.

Turning now to FIG. 12, an illustration of an inspection environment is depicted in accordance with an illustrative embodiment. Inspection environment 1200 may be a physical implementation of inspection environment 200 of FIG. 2. Inspection environment 1200 includes x-ray inspection equipment 1202. X-ray inspection equipment 1202 may be a physical implementation of x-ray inspection equipment 202 of FIG. 2.

X-ray inspection equipment 1202 includes x-ray generation system 1204 and detector system 1206. X-ray generation system 1204 may take the form of scintillator 1208 which is associated with detector system 1206. X-rays 1210 generated by x-ray generation system 1204 may travel between detectors of detector system 1206 and towards workpiece 1212.

Backscatter 1214 may result from x-rays 1210 reaching workpiece 1212. Backscatter 1214 may be received by detector system 1206. Detector system 1206 may generate data based on backscatter 1214. The data generated based on backscatter 1214 may be used to determine if workpiece 1212 has any out of tolerance conditions.

The illustrations of inspection environments in FIGS. 2 and 12, a standard in FIG. 3, images in FIGS. 4, 5, and 10, a plot profile in FIG. 6, a ratio plot in FIG. 7, a workpiece in FIGS. 8 and 9, and computer system in FIG. 11 are not meant to imply physical or architectural limitations to the manner in which an illustrative embodiment may be implemented. Other components in addition to or in place of the ones illustrated may be used. Some components may be optional. Also, the blocks are presented to illustrate some functional components. One or more of these blocks may be combined, divided, or combined and divided into different blocks when implemented in an illustrative embodiment.

For example, number of fasteners 222 may include a greater number of fasteners than just first fastener 246 and second fastener 250. As another example, workpiece 206 may include a greater number of objects than first object 226 and second object 228. As yet a further example, plot profile 261 may have a greater number of valleys other than just valley 266. For example, plot profile 261 may have two valleys, each of which are associated with the same fastener. As another example, plot profile 261 may have three valleys, each of which are associated with the same fastener. In other examples, plot profile 261 may have more than three valleys, in which at least two fasteners are represented in plot profile 261.

Figure 13:
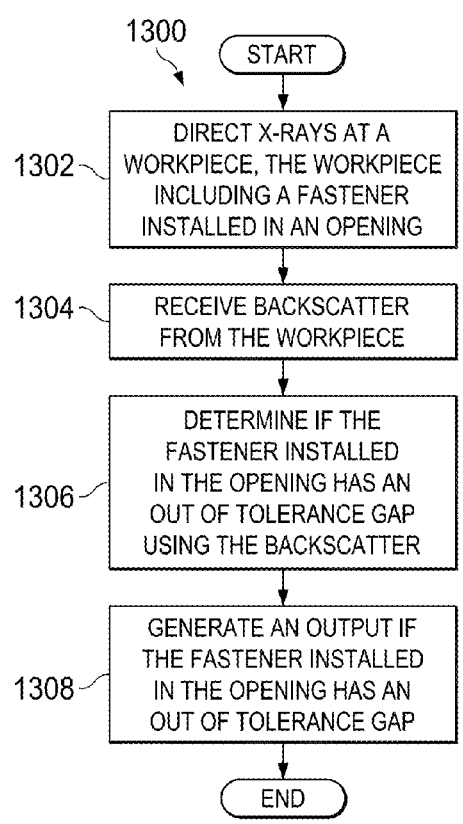
FIG. 13 is an illustration of a process for detecting an out of tolerance gap between a fastener and an opening in the form of a flowchart in accordance with an illustrative embodiment.

Turning now to FIG. 13, an illustration of a process for detecting an out of tolerance gap between a fastener and an opening in the form of a flowchart is depicted in accordance with an illustrative embodiment. Process 1300 may begin by directing x-rays at a workpiece, the workpiece including a fastener installed in an opening (operation 1302). In some illustrative examples, the fastener may be selected from at least one of a bolt, a rivet, or other desirable fastener. Backscatter from the workpiece may be received (operation 1304). It may be determined if the fastener installed in the opening has an out of tolerance gap using the backscatter (operation 1306). In some illustrative examples, determining if the fastener installed in the opening has an out of tolerance gap using the backscatter comprises creating a plot profile for a location through the fastener using the backscatter; determining a lowest value in a valley of the plot profile; and determining if the fastener installed in the opening has an out of tolerance gap using the lowest value in the valley of the plot profile.

In some illustrative examples, determining if the fastener installed in the opening has an out of tolerance gap using the lowest value in the valley of the plot profile may comprise calculating a difference between the lowest value and a background; determining if the difference is above a limit; and determining that the fastener installed in the opening has an out of tolerance gap if the difference is above the limit. In other illustrative examples, determining if the fastener installed in the opening has an out of tolerance gap using the lowest value in the valley of the plot profile may comprise calculating a difference between the lowest value and a background; determining a ratio value between the difference and the background; determining an estimated gap using the ratio value; and determining if the estimated gap is an acceptable size to determine if the fastener installed in the opening has an out of tolerance gap. In other illustrative examples, determining if the fastener installed in the opening has an out of tolerance gap using the lowest value in the valley of the plot profile may comprise determining if the lowest value in the valley of the plot profile is below a limit; and determining that the fastener installed in the opening has an out of tolerance gap if the lowest value is below the limit.

An output may be generated if the fastener installed in the opening has an out of tolerance gap (operation 1308). An output may take the form of an email, a text, an indicator light, an indicator message, an alarm, or other desirable output. Afterwards, the process terminates.

Another illustrative example of a process for detecting an out of tolerance gap between a fastener and an opening may begin by inspecting a standard to form standardized data. The standardized data may include an image, a limit, a background, a ratio equation, or other desirable data based on the inspection of the standard. The standardized data may also be formed using direct measurements of the diameters of a number of fasteners and a number of openings of the standard.

X-rays may be directed at a workpiece, the workpiece including a fastener installed in an opening. The workpiece may have substantially the same material makeup as the standard. Backscatter may be received from the workpiece. The backscatter may be received in response to the x-rays.

It may be determined whether the fastener installed in the opening has an out of tolerance gap using the backscatter and the standardized data. For example, an image of the workpiece formed from the backscatter may be compared to an image of the standard. As another example, a plot profile for the workpiece may be formed using the backscatter. A lowest point in a valley of the plot profile may be compared to a limit set based on the standard. As a further example, a ratio may be determined for the workpiece. The ratio may be input into a ratio to estimated gap equation calculated based on the standard.

An output may be generated if the fastener installed in the opening has an out of tolerance gap. An output may take the form of an email, a text, an indicator light, an indicator message, an alarm, or other desirable output. Afterwards, the process terminates. The standard may have a number of out of tolerance gaps. In these illustrative examples, a ratio to gap size equation may be created based on the standardized data.

Another illustrative example of a process for detecting an out of tolerance gap between a fastener and an opening may be presented. The illustrative example may begin by directing x-rays at a workpiece, the workpiece including a fastener installed in an opening. The fastener may take the form of a bolt, a rivet, or other desirable fastener. Backscatter may be received from the workpiece. In some illustrative examples, directing the x-rays at the workpiece includes directing the x-rays at a first side of the workpiece. In some illustrative examples, receiving the backscatter from the workpiece includes receiving the backscatter on the first side of the workpiece. The backscatter may be formed by the workpiece in response to the x-rays.

An image may be formed of the fastener installed in the opening using the backscatter. In some illustrative examples, forming the image of the fastener installed in the opening comprises forming a raw data image with contrast adjustment and performing a simple bandpass filter on the raw data image to form the image.

A plot profile for a location through the fastener in the image may be created. A lowest value in a valley of the plot profile may be determined. It may be determined if the lowest value in the valley of the plot profile is an acceptable value. In some illustrative examples, determining if the lowest value in the valley of the plot profile is an acceptable value comprises calculating a difference between the lowest value and a background; determining if the difference is above a limit; and determining that lowest value in the valley of the plot profile is not an acceptable value if the difference is above the limit. In some illustrative examples, the background may be generated from a standard having a same material layup as the workpiece.

In some illustrative examples, the background may be a value determined from backscatter from an area of the workpiece not containing the fastener installed in the opening. In some illustrative examples, determining if the lowest value in the valley of the plot profile is an acceptable value comprises calculating a difference between the lowest value and a background; determining a ratio value between the difference and the background; determining an estimated gap using the ratio value; determining if the estimated gap is an acceptable size; and determining that the lowest value in the valley of the plot profile is not an acceptable value if the estimated gap is not an acceptable size. In some illustrative examples, determining if the lowest value in the valley of the plot profile is an acceptable value comprises determining if the lowest value in the valley of the plot profile is below a limit; and determining that the lowest value in the valley of the plot profile is not an acceptable value if the lowest value is below the limit.

An output indicating an out of tolerance gap may be generated if the lowest value in the valley of the plot profile is not an acceptable value. An output may take the form of an email, a text, an indicator light, an indicator message, an alarm, or other desirable output. Afterwards, the process terminates.

The flowcharts and block diagrams in the different depicted embodiments illustrate the architecture, functionality, and operation of some possible implementations of apparatus and methods in an illustrative embodiment. In this regard, each block in the flowcharts or block diagrams may represent a module, a segment, a function, and/or a portion of an operation or step. For example, one or more of the blocks may be implemented as program code, in hardware, or a combination of the program code and hardware. When implemented in hardware, the hardware may, for example, take the form of integrated circuits that are manufactured or configured to perform one or more operations in the flowcharts or block diagrams.

In some alternative implementations of an illustrative embodiment, the function or functions noted in the blocks may occur out of the order noted in the figures. For example, in some cases, two blocks shown in succession may be executed substantially concurrently, or the blocks may sometimes be performed in the reverse order, depending upon the functionality involved. Also, other blocks may be added in addition to the illustrated blocks in a flowchart or block diagram.

For example, process 1300 may further comprise forming an image of the fastener installed in the opening using the backscatter. In this illustrative example, creating the plot profile for the location through the fastener may comprise creating a plot profile for a location through the fastener in the image. In some illustrative examples, creating a plot profile for a location through the fastener using the backscatter comprises creating the plot profile for the location through the fastener using the image. In some illustrative examples, in process 1300, forming the image of the fastener installed in the opening comprises forming a raw data image with contrast adjustment and performing a simple bandpass filter on the raw data image to form the image.

Figure 14:
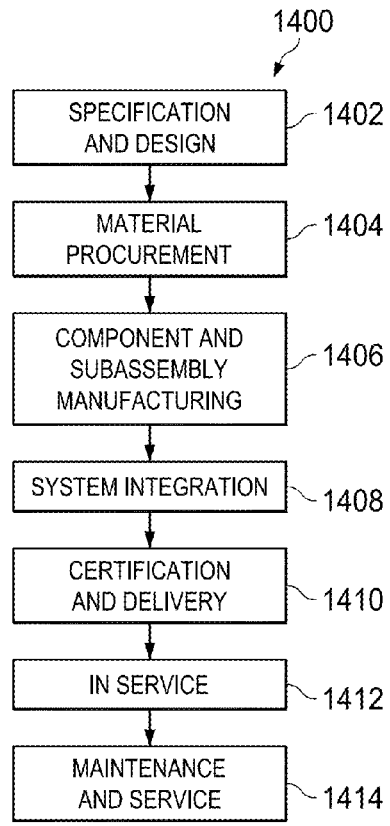
FIG. 14 is an illustration of an aircraft manufacturing and service method in the form of a block diagram in accordance with an illustrative embodiment.
Figure 15:
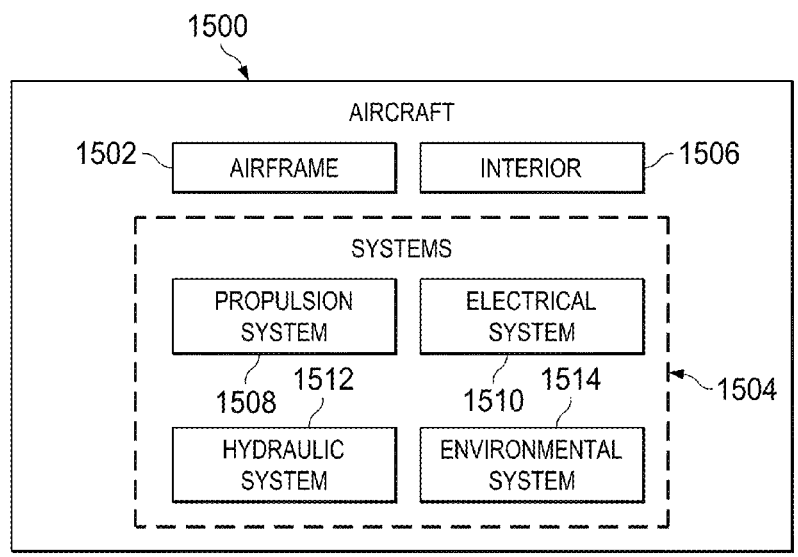
FIG. 15 is an illustration of a block diagram of an aircraft in which an illustrative embodiment may be implemented.

The illustrative embodiments of the disclosure may be described in the context of aircraft manufacturing and service method 1400 as shown in FIG. 14 and aircraft 1500 as shown in FIG. 15. Turning first to FIG. 14, an illustration of a block diagram of an aircraft manufacturing and service method is depicted in accordance with an illustrative embodiment. During pre-production, aircraft manufacturing and service method 1400 may include specification and design 1402 of aircraft 1500 in FIG. 15 and material procurement 1404.

During production, component and subassembly manufacturing 1406 and system integration 1408 of aircraft 1500 in FIG. 15 take place. Thereafter, aircraft 1500 in FIG. 15 may go through certification and delivery 1410 in order to be placed in service 1412. While in service 1412 by a customer, aircraft 1500 in FIG. 15 is scheduled for routine maintenance and service 1414, which may include modification, reconfiguration, refurbishment, and other maintenance or service.

Each of the processes of aircraft manufacturing and service method 1400 may be performed or carried out by a system integrator, a third party, and/or an operator. In these examples, the operator may be a customer. For the purposes of this description, a system integrator may include, without limitation, any number of aircraft manufacturers and major-system subcontractors; a third party may include, without limitation, any number of vendors, subcontractors, and suppliers; and an operator may be an airline, a leasing company, a military entity, a service organization, and so on.

With reference now to FIG. 15, an illustration of a block diagram of an aircraft is depicted in which an illustrative embodiment may be implemented. In this example, aircraft 1500 is produced by aircraft manufacturing and service method 1400 in FIG. 14 and may include airframe 1502 with plurality of systems 1504 and interior 1506. Examples of systems 1504 include one or more of propulsion system 1508, electrical system 1510, hydraulic system 1512, and environmental system 1514. Any number of other systems may be included. Although an aerospace example is shown, different illustrative embodiments may be applied to other industries, such as the automotive industry.

The apparatus and methods embodied herein may be employed during at least one of the stages of aircraft manufacturing and service method 1400 in FIG. 14. One or more illustrative embodiments may be used during component and subassembly manufacturing 1406. For example, workpiece 206 may be a portion of aircraft 1500 which is inspected using x-ray inspection equipment 202 of FIG. 2 during component and subassembly manufacturing 1406. As another example, workpiece 206 may be a portion of aircraft 1500 which is inspected using x-ray inspection equipment 202 of FIG. 2 during maintenance and service 1414.

A method and apparatus for determining if a fastener installed in an opening has an out of tolerance gap is presented. There are a large number of fasteners in the exterior of an aircraft. These fasteners may join the aircraft skin panels to a backing structure. The aircraft skin may be part of a primary load bearing structure. As a result, the interface conditions between the fasteners and the skin and backing structure have desirable interference and clearance conditions. Oversized or double drilled openings can weaken the integrity of the structure. This weakening may be present initially or with increased flight hours.

Once fasteners have been installed in openings in the aircraft skin, conventional measurements may require removing the fasteners to measure the size and form of the openings as well as the sizes of the fasteners. The fasteners may not be accessible or may be difficult to access. As a result, disassembly of portions of the aircraft may be required to directly measure the size of the openings and the sizes of the fasteners. Further, for conventional non-destructive inspection, access to both sides of a workpiece may be required or desirable. To inspect fasteners within openings in the aircraft skin panels using conventional non-destructive inspection techniques, disassembly of the aircraft may be required. For example, transmission radiography can be used to measure fasteners and openings without removing the fasteners. However, transmission radiography requires access to the back side of the fastener to place a film or detector. Further, the alignment of both the film and the x-ray source is critical in transmission radiography to ensure the x-rays travel along the direction of the fastener.

Disassembly of portions of the aircraft may have undesirable costs. Further, disassembly may also have the potential for maintenance induced inconsistencies.

The presented method and apparatus may use non-destructive inspection equipment to identify an out of tolerance gap. The method and apparatus may allow for identifying out of tolerance conditions with one-sided access. Further, the method and apparatus may allow for identifying out of tolerance conditions without disassembly. In some illustrative examples, the method and apparatus may quantify a size of a gap between a fastener and a hole. A quantitative analysis of the condition of the fastener and opening may indicate the severity of a misdrill. Knowing the size of a gap between a fastener and a hole may aid in determining a next-step.

The presented method may use backscatter x-ray imaging systems to identify out of tolerance gaps although it was previously believed that gaps present between interference fit fasteners and their corresponding openings were below the spatial resolution of backscatter x-ray imaging systems. The illustrative embodiments take advantage of edge effects of the x-rays interacting with the mating surfaces of the fasteners and the openings to enhance the contrast of the features of interest.

The presented method and apparatus may reduce the time to inspect a workpiece. Further, the presented method and apparatus may reduce the time for maintenance of an aircraft. By reducing the time to inspect a workpiece, the readiness of the aircraft may be increased. An aircraft is not available for flight while it is being inspected, disassembled, or reassembled. By decreasing the time an aircraft is down for inspection and maintenance, aircraft readiness may be increased.

A standard having a substantially similar material makeup to a number of workpieces is used to create standardized data. The number of workpieces may be inspected. The resulting inspection data may be compared to the standardized data to determine if an out of tolerance condition is present. An out of tolerance condition may be present if a black or substantially black ring is viewed in an image of the workpiece formed from backscatter data. An out of tolerance condition may be present if a pixel has a gray value below a limit in a plot profile. The pixel may be a lowest point of a valley in the plot profile. An out of tolerance condition may be present if a difference between a gray value of a pixel and a gray value of a background is above a limit. The pixel may be a lowest point of a valley in the plot profile.

Further, the resulting inspection data may be compared to the standardized data to determine an estimated gap size. To determine an estimated gap size, a ratio value may be inputted into an equation determined using the standard. The ratio value may be determined using a gray value of a pixel and a gray value of a background. The pixel may be a lowest point of a valley in the plot profile.

Although the illustrative examples have been described in relation to fasteners and openings, the method and apparatus may be used in relation to other gaps. The method and apparatus may be used to inspect gaps which are not associated with fasteners. For example, the presented method and apparatus may be used to inspect a gap between a first part and a second part.

The description of the different illustrative embodiments has been presented for purposes of illustration and description, and is not intended to be exhaustive or limited to the embodiments in the form disclosed. Many modifications and variations will be apparent to those of ordinary skill in the art.

Further, different illustrative embodiments may provide different features as compared to other desirable embodiments. The embodiment or embodiments selected are chosen and described in order to best explain the principles of the embodiments, the practical application, and to enable others of ordinary skill in the art to understand the disclosure for various embodiments with various modifications as are suited to the particular use contemplated.

What is claimed is:

1. A method comprising:
   directing x-rays at a workpiece, the workpiece including a fastener installed in an opening;

receiving backscatter from the workpiece;
determining if the fastener installed in the opening has an out of tolerance gap using the backscatter; and
generating an output if the fastener installed in the opening has the out of tolerance gap.

2. The method of claim 1, wherein determining if the fastener installed in the opening has the out of tolerance gap using the backscatter comprises:
creating a plot profile for a location through the fastener using the backscatter;
determining a lowest value in a valley of the plot profile; and
determining if the fastener installed in the opening has the out of tolerance gap using the lowest value in the valley of the plot profile.

3. The method of claim 2, wherein determining if the fastener installed in the opening has the out of tolerance gap using the lowest value in the valley of the plot profile comprises:
calculating a difference between the lowest value and a background;
determining if the difference is above a limit; and
determining that the fastener installed in the opening has the out of tolerance gap if the difference is above the limit.

4. The method of claim 2, wherein determining if the fastener installed in the opening has the out of tolerance gap using the lowest value in the valley of the plot profile comprises:
calculating a difference between the lowest value and a background;
determining a ratio value between the difference and the background;
determining an estimated gap using the ratio value; and
determining if the estimated gap is an acceptable size to determine if the fastener installed in the opening has the out of tolerance gap.

5. The method of claim 4, wherein the background is generated from a standard having a same material layup as the workpiece.

6. The method of claim 4, wherein the background is a value determined from backscatter from an area of the workpiece not containing the fastener installed in the opening.

7. The method of claim 2, wherein determining if the fastener installed in the opening has the out of tolerance gap using the lowest value in the valley of the plot profile comprises:
determining if the lowest value in the valley of the plot profile is below a limit; and
determining that the fastener installed in the opening has the out of tolerance gap if the lowest value is below the limit.

8. The method of claim 7, wherein the limit is set based on a standard having a same material layup as the workpiece.

9. The method of claim 2, further comprising:
forming an image of the fastener installed in the opening using the backscatter; and
wherein creating the plat profile for the location through the fastener comprises creating the plat profile for the location through the fastener in the image.

10. The method of claim 9, wherein forming the image of the fastener installed in the opening comprises:
forming a raw data image with contrast adjustment; and
performing a simple bandpass filter on the raw data image to form the image.

11. The method of claim 10, wherein creating the plot profile for the location through the fastener using the backscatter comprises:
creating the plot profile for the location through the fastener using the image.

12. The method of claim 1, further comprising:
inspecting a standard to form standardized data, wherein determining if the fastener installed in the opening has the out of tolerance gap also uses the standardized data.

13. The method of claim 12, wherein the standard has a number of out of tolerance gaps and further comprising:
creating a ratio to gap size equation based on the standardized data.

14. The method of claim 1, wherein directing the x-rays at the workpiece includes directing the x-rays at a first side of the workpiece, and wherein receiving the backscatter from the workpiece includes receiving the backscatter on the first side of the workpiece.

15. A method comprising:
directing x-rays at a workpiece, the workpiece including a fastener installed in an opening;
receiving backscatter from the workpiece; and
determining an estimated gap associated with the fastener in the opening using the backscatter.

16. The method of claim 15, wherein determining the estimated gap comprises:
creating a plot profile for a location through the fastener using the backscatter.

17. The method of claim 16, wherein determining the estimated gap further comprises:
determining a lowest value in a valley of the plot profile;
determining a difference between the lowest value and a background;
determining a ratio value between the difference and the background; and
determining the estimated gap using the ratio value.

18. An apparatus comprising:
x-ray inspection equipment having an x-ray generation system for directing x-rays at a workpiece, the workpiece including a fastener installed in an opening, and a detector system for receiving backscatter from the workpiece; and
a processor unit for determining if the fastener installed in the opening has an out of tolerance gap using the backscatter, and generating an output if the fastener installed in the opening has the out of tolerance gap.
a processor unit for determining if the fastener installed in the opening has an out of tolerance gap using the backscatter, and generating an output if the fastener installed in the opening has the out of tolerance gap.

19. The apparatus of claim 18, wherein in determining if the fastener installed in the opening has the out of tolerance gap using the backscatter, the processor unit creates a plot profile for a location through the fastener using the backscatter; determines a lowest value in a valley of the plot profile; and determines if the fastener installed in the opening has the out of tolerance gap using the lowest value in the valley of the plot profile.

20. The apparatus of claim 19, wherein in determining if the fastener installed in the opening has the out of tolerance gap using the lowest value in the valley of the plot profile, the processor unit calculates a difference between the lowest value and a background; determines a ratio value between the difference and the background; determines an estimated gap using the ratio value; and determines if the estimated gap is an acceptable size to determine if the fastener installed in the opening has the out of tolerance gap.

* * * * *

UNITED STATES PATENT AND TRADEMARK OFFICE
CERTIFICATE OF CORRECTION

PATENT NO.       : 9,689,813 B2
APPLICATION NO.  : 14/633379
DATED            : June 27, 2017
INVENTOR(S)      : Lou et al.

Page 1 of 1

It is certified that error appears in the above-identified patent and that said Letters Patent is hereby corrected as shown below:

Column 29, Lines 60 to 62, each reference of "plat" in Claim 9 should be "plot"

Signed and Sealed this
Sixth Day of November, 2018

Andrei Iancu
*Director of the United States Patent and Trademark Office*